(12) United States Patent
Nelson et al.

(10) Patent No.: US 11,684,377 B2
(45) Date of Patent: Jun. 27, 2023

(54) JOINT RESECTION GUIDE

(71) Applicant: Howmedica Osteonics Corp., Mahwah, NJ (US)

(72) Inventors: Andrew J. Nelson, New City, NY (US); Daniel E. Sapio, Mohegan Lake, NY (US); Sunny Shorabh, Ghaziabad (IN); Shashank Verma, Agra (IN); Morgan Schliem, Hoboken, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 73 days.

(21) Appl. No.: 17/154,321

(22) Filed: Jan. 21, 2021

(65) Prior Publication Data
US 2021/0219995 A1   Jul. 22, 2021

Related U.S. Application Data

(60) Provisional application No. 62/964,153, filed on Jan. 22, 2020.

(51) Int. Cl.
*A61B 17/17* (2006.01)

(52) U.S. Cl.
CPC ...... *A61B 17/1739* (2013.01); *A61B 17/1735* (2013.01)

(58) Field of Classification Search
CPC . A61B 17/15; A61B 17/1735; A61B 17/1739; A61B 17/1778; A61B 17/155; A61B 17/157
See application file for complete search history.

(56) References Cited

U.S. PATENT DOCUMENTS

| | | | |
|---|---|---|---|
| RE34,985 E * | 6/1995 | Pennig | A61B 17/6416 606/57 |
| 6,642,686 B1 * | 11/2003 | Ruch | A61B 34/76 318/568.14 |
| 6,672,788 B2 * | 1/2004 | Hathaway | F16C 11/0619 403/90 |
| 7,794,467 B2 | 9/2010 | McGinley et al. | |
| 2007/0123896 A1 | 5/2007 | Wyss et al. | |

FOREIGN PATENT DOCUMENTS

EP   634146 A2 *  1/1995  ....... A61B 17/32002

* cited by examiner

*Primary Examiner* — Anu Ramana
(74) *Attorney, Agent, or Firm* — Lerner David LLP

(57) ABSTRACT

A resection guide includes an anchor having bone anchoring features, a cutting block having a cutting guide defined therein, and a linkage flexibly connecting the cutting block to the anchor. The flexibility of the linkage provides the cutting block with six degrees of freedom of motion relative to the anchor.

17 Claims, 20 Drawing Sheets

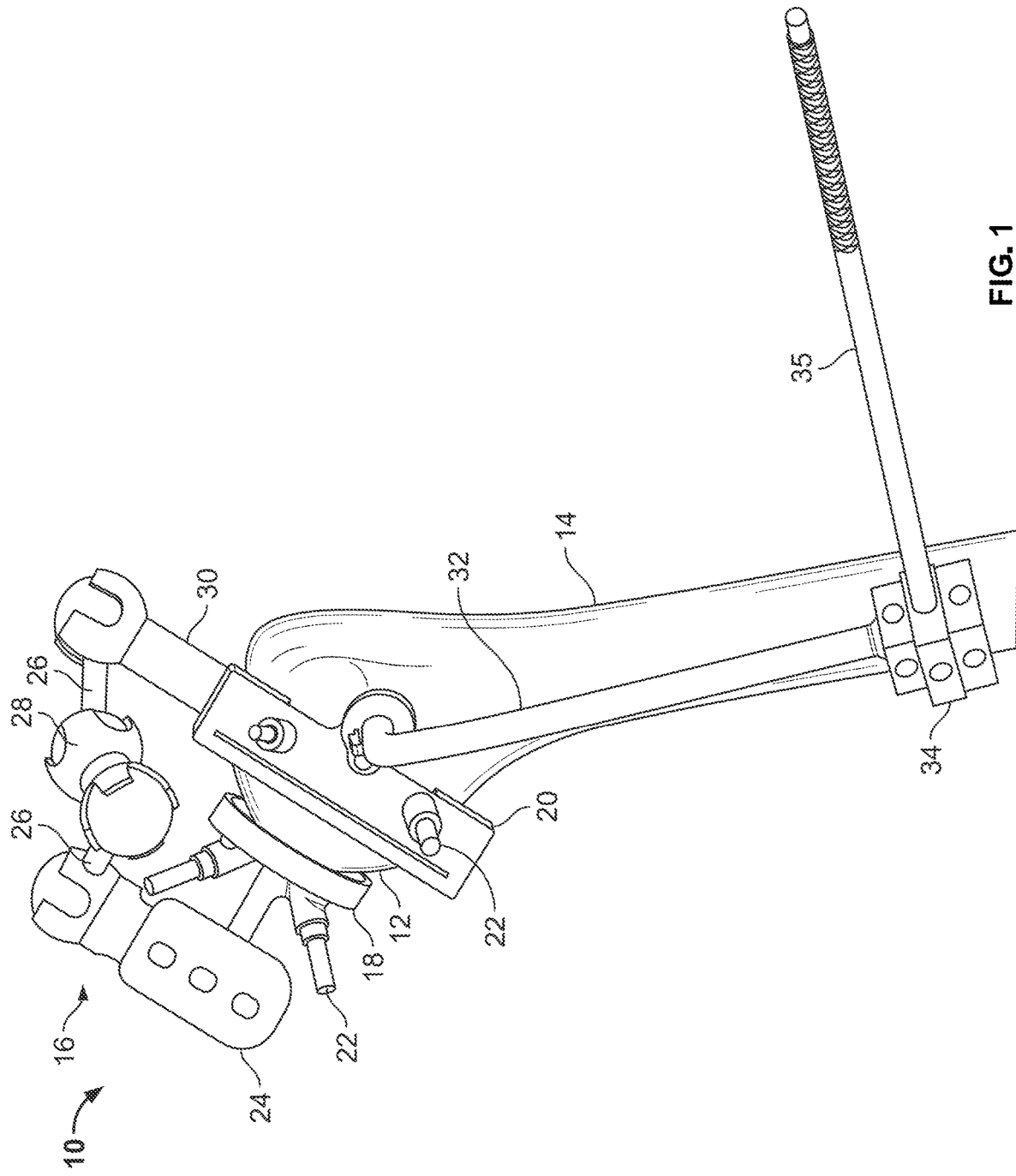

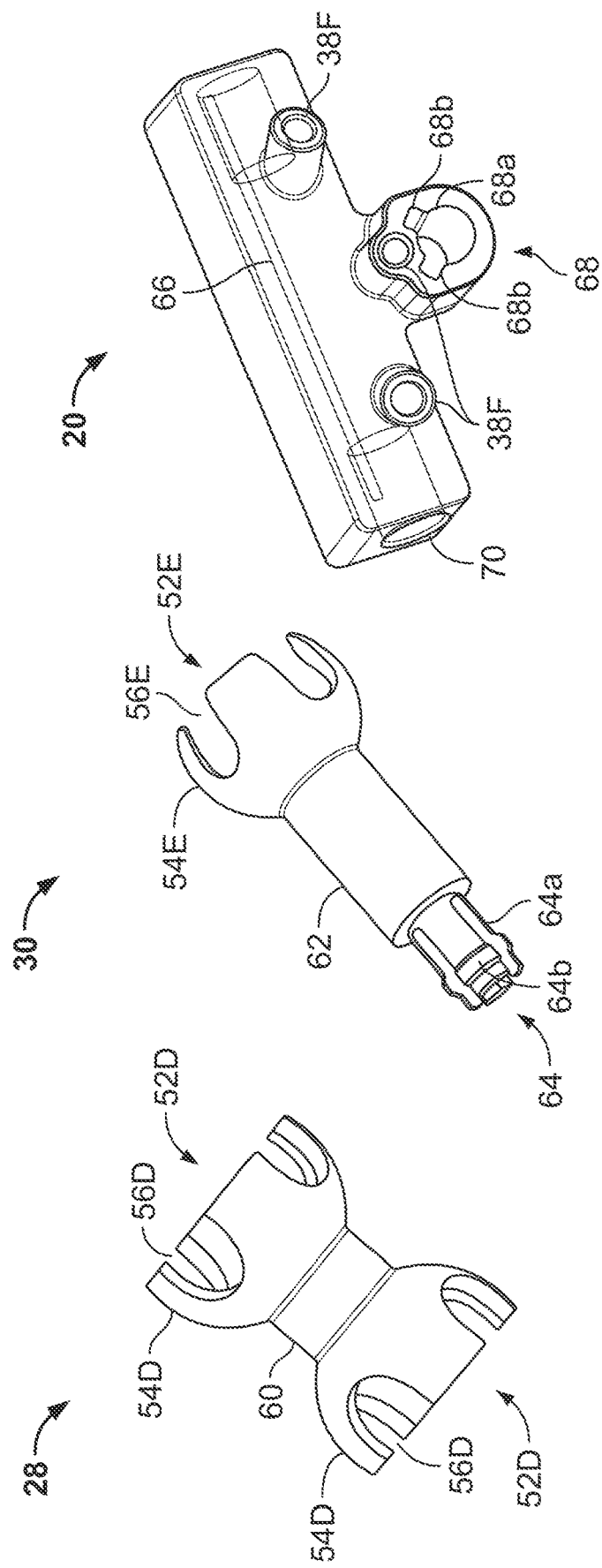

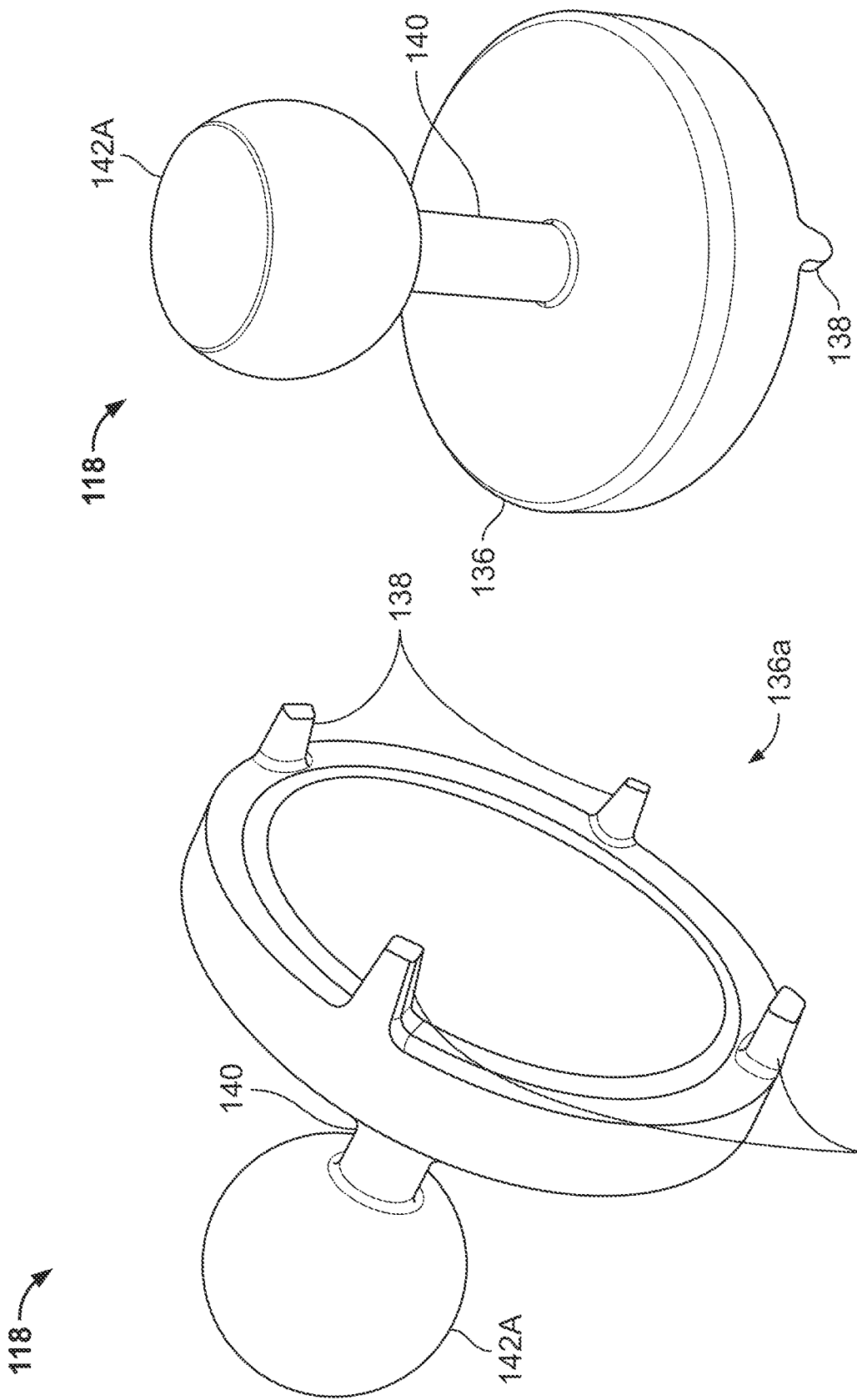

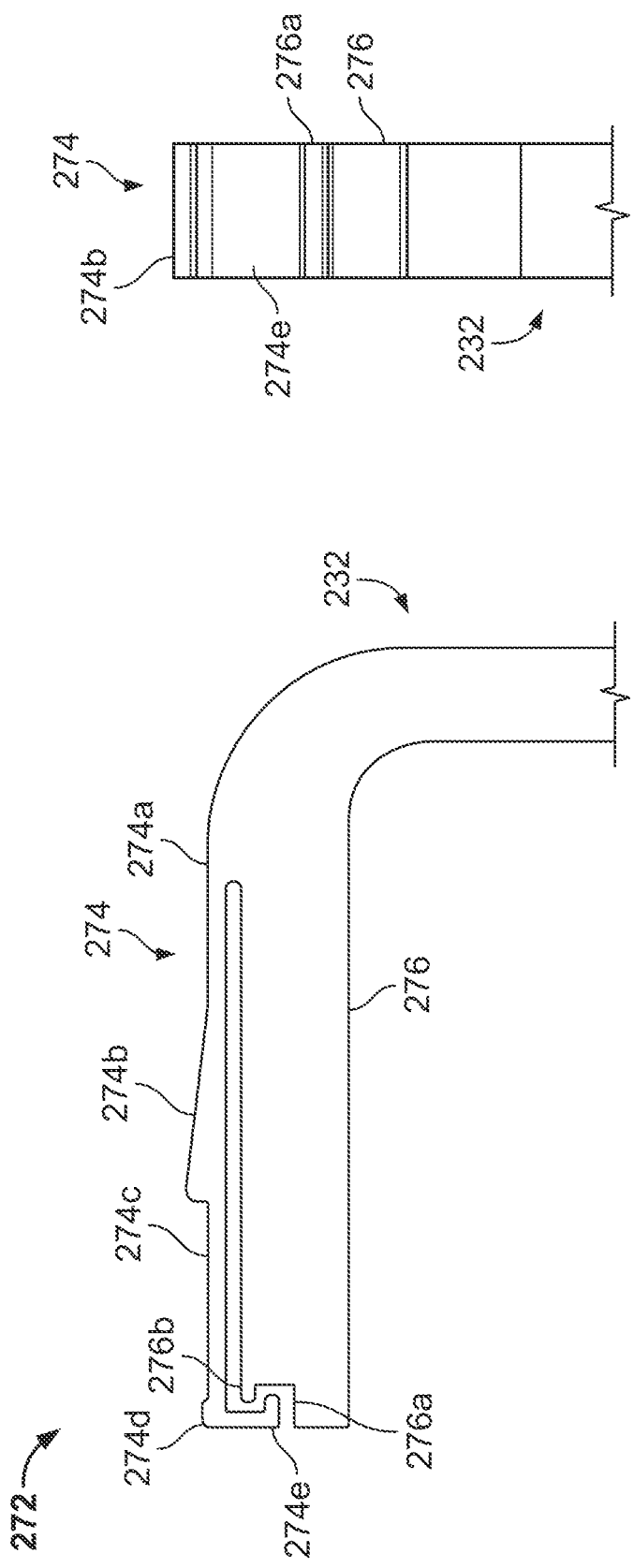

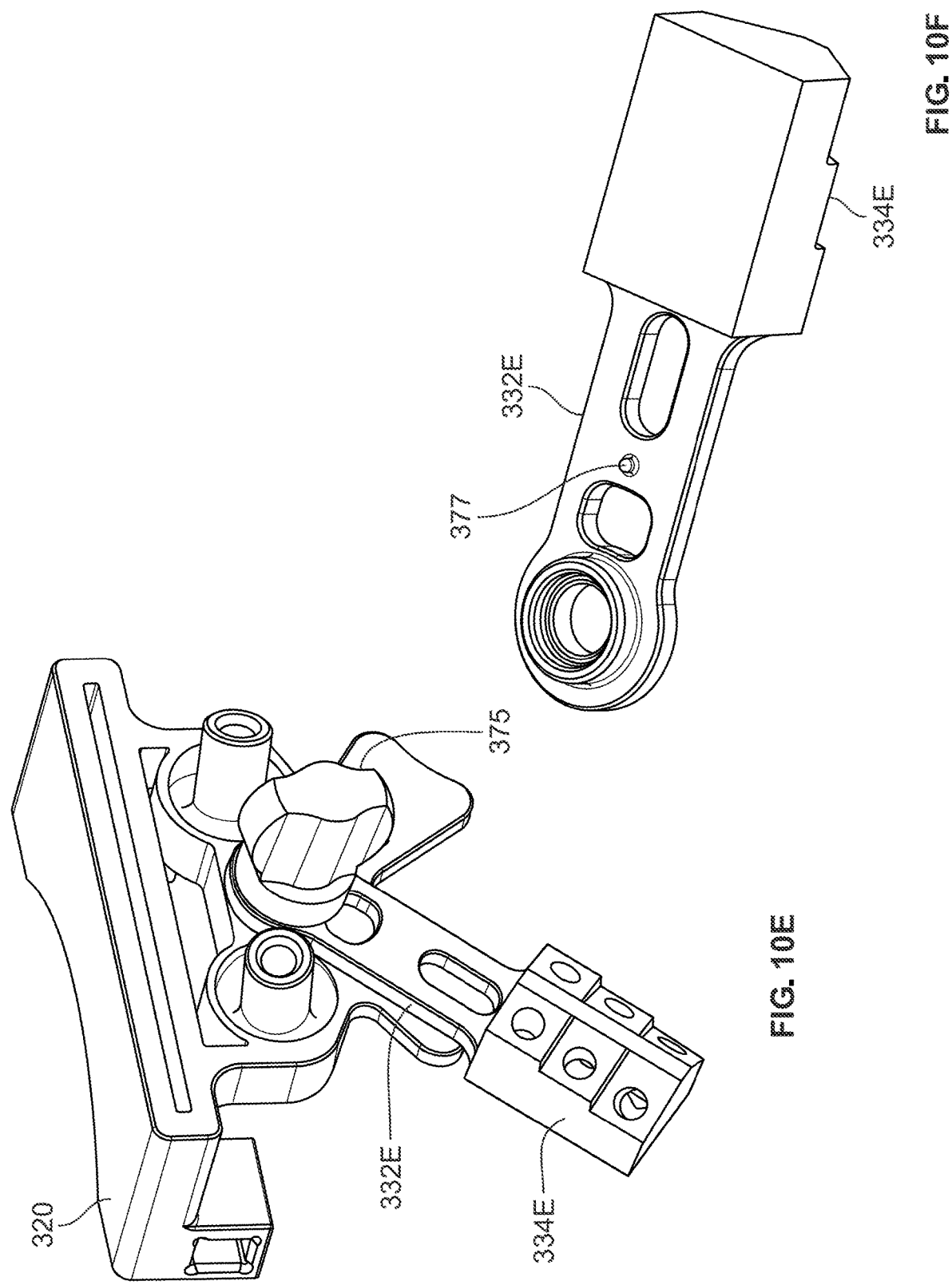

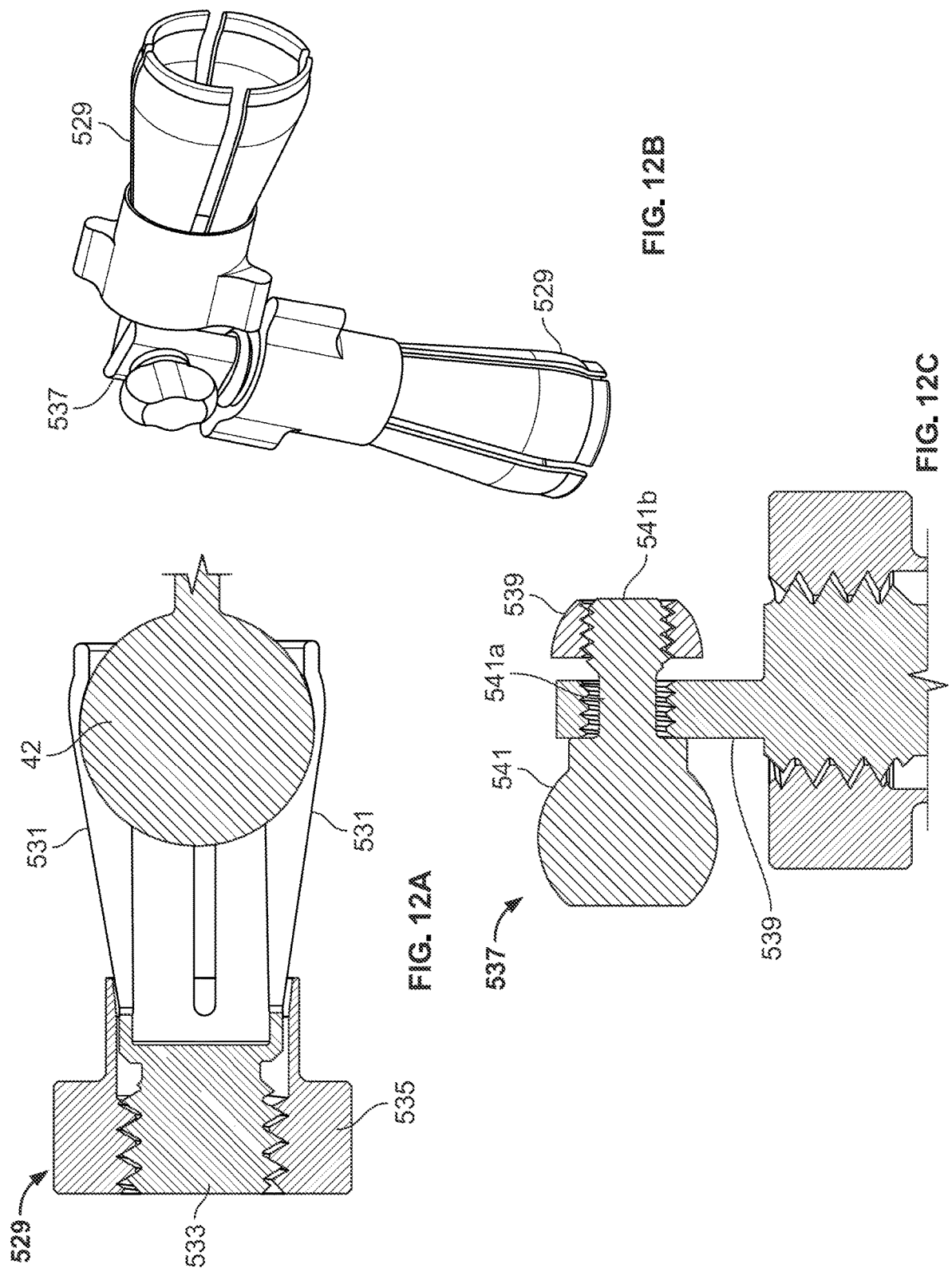

JOINT RESECTION GUIDE

CROSS-REFERENCE TO RELATED APPLICATION

The present application claims the benefit of the filing date of U.S. Provisional Patent Application No. 62/964,153 filed Jan. 22, 2020, the disclosure of which is hereby incorporated herein by reference.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in the case where tendons in a joint become lax or soft tissues in or adjacent the joint tear become damaged or worn.

Arthroplasty procedures can be used to repair damaged joints. During a typical arthroplasty procedure, an arthritic or otherwise dysfunctional joint can be remodeled or realigned, or an implant or implants can be implanted into the damaged region. Arthroplasty procedures may take place in any of a number of different regions of the body, such as a knee, a hip, a shoulder, or an elbow.

One type of arthroplasty procedure is a shoulder arthroplasty, in which a damaged shoulder joint is replaced with prosthetic implants. The shoulder joint may have been damaged by, for example, arthritis (e.g., severe osteoarthritis or degenerative arthritis), trauma, or a rare destructive joint disease.

Implants that are implanted into a damaged region may provide support and structure to the damaged region, and may help to restore the damaged region, thereby enhancing its functionality. Prior to implantation of an implant in a damaged region, the damaged region may be prepared to receive the implant. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant. Standard alignment instrumentation may be used for locating a position and orientation to resect the humeral head for proper humeral implant placement in the humerus.

Accuracy in implant alignment is an important factor to the success of the procedure. A one to two millimeter translational misalignment, or a one to two degree rotational misalignment, may result in imbalanced ligaments, and may thereby significantly affect the outcome of the procedure. For example, implant misalignment may result in intolerable post-surgery pain, and also may prevent the patient from having proper deltoid tension or range of motion.

To achieve accurate implant alignment, prior to treating (e.g., cutting, drilling, reaming, and/or resurfacing) any regions of a bone, it is important to correctly determine the location at which the treatment will take place and how the treatment will be oriented. Currently available instrument and tools do not always enable the surgeon to make the most accurate cuts on the bone surface in preparing the target joint for implantation. Thus, there remains a need for tools that improve the accuracy of the joint resurfacing process.

BRIEF SUMMARY

In accordance with an aspect of the present disclosure, a modular linkage may be used to position a cutting guide for a resection. The resection may be a humeral head resection. Alternatively, the modular linkage may be used to position various elements for other procedures. A surgeon or user may be provided with an assortments of links or modular parts. The links may include an anchor able to secured to bone, a cutting block including a cutting guide, which may be a slot, and a number of modular and pivotably interconnectable intermediate links. Some or all of the links may have reversible connection features that allow relative motion between connected links, such as, for example, a ball and a socket for forming ball and socket joints between the links. In aggregate, the pivotable connections between the links may create a flexible linkage. The connections may have enough friction to prevent, or at least slow, flexure of a linkage of typical length in the absence of active manipulation by the surgeon. For example, the connections may have sufficient internal friction to suspend the anchor at a given position while only supported by the fixation of the anchor to the bone despite the force of gravity if the linkage is of a typical length. Typical linkage lengths may be from three to nine links, including an anchor and a cutting block.

A method of using the modular linkage may include determining an appropriate number and type of links based upon a surgical procedure to be performed and details of the patient's anatomy. An anchor may be fixed to the patient's bone. For example, the anchor may be fixed to a portion of the patient's bone that is to be removed by the resection. A linkage may be assembled from the selected links before or after fixation of the anchor to the patient's bone. One or more rods may be keyed to the cutting block to aid relative positioning of the patient's arm and the cutting block. The cutting block may be positioned near the bone to be cut and on the intended resection plane, and the patient's arm may be aligned with the one or more rods. After the cutting block and arm are properly positioned, the cutting block may be fixed to the bone. A resection may be performed through the cutting guide in the cutting block. The anchor may or may not be removed from the bone, and the cutting block may be disconnected from the rest of the linkage, after the cutting block is fixed to the bone and before or after the resection is performed.

In another aspect, a resection guide includes an anchor having bone anchoring features, a cutting block having a cutting guide defined therein, and a linkage flexibly connecting the cutting block to the anchor such that the anchor has six degrees of freedom of motion relative to the anchor.

In some arrangements according to any of the foregoing, flexibility of the linkage includes internal friction enabling the linkage to suspend the cutting block in opposition to gravity.

In some arrangements according to any of the foregoing, the linkage may include a chain of interconnected rigid links, each rigid link within the chain being of the same type and including both a round element and a socket configured to rotatably receive one of the round elements.

In some arrangements according to any of the foregoing, the linkage may include a link that further includes a plurality of flexible leaves defining a socket therebetween and a tightening element that is movable relative to the leaves to tighten the socket.

In some arrangements according to any of the foregoing, the cutting guide may include a plurality of index holes at different positions relative to an aperture, and wherein the guide further comprises an alignment rod including an end engageable to the aperture and a boss engageable to one of the index holes In some arrangements according to any of the foregoing, the linkage includes a plurality of interconnected rigid links.

In some arrangements according to any of the foregoing, at least two of the plurality of rigid links are interconnected by a ball and socket joint.

In some arrangements according to any of the foregoing, the ball and socket joint includes a plurality of tabs for retaining the ball.

In some arrangements according to any of the foregoing, the tabs are elastically flexible such that the ball may be reversibly inserted into and removed from retention by the tabs.

In some arrangements according to any of the foregoing, the plurality of rigid links includes at least a first type of link and a second type of link, wherein the first type of link differs from the second type of link.

In some arrangements according to any of the foregoing, the first type of link is modularly connectable to the second type of link, but the first type of link is not modularly connectable to another of the first type of link.

In some arrangements according to any of the foregoing, the first type of link is a barbell including a bar having two ends and a ball on each of the two ends of the bar.

In some arrangements according to any of the foregoing, the second type of link includes at least one socket.

In some arrangements according to any of the foregoing, the second type of link is a slider including a track defined by an element having a partial cylinder shape, the partial cylinder shape having an internal diameter providing an interference fit with either ball of the barbell.

In some arrangements according to any of the foregoing, a first link includes a peg and a second link includes a bore sized to have an interference fit with the peg.

In some arrangements according to any of the foregoing, the resection guide includes an alignment rod connectable to the cutting block.

In some arrangements according to any of the foregoing, the cutting block includes a connecting element whereby the alignment rod is connectable to the cutting block, the connecting element defining at least one discrete connected position for the alignment rod relative to the cutting block corresponding to an intended resection angle relative to a longitudinal axis of a bone to be cut.

In some arrangements according to any of the foregoing, the connecting element is a cylindrical through-bore with two channels extending therefrom at equal but opposite angles relative to the cutting block, and the alignment rod includes a keyed portion, the keyed portion further including a key extending therefrom and insertable into the channels such that a connected position for the alignment rod relative to the cutting block wherein the ridge is inserted into either of the channels corresponds to the intended resection angle relative to the longitudinal axis of the bone to be cut.

In some arrangements according to any of the foregoing, the connecting element is a V-shaped aperture with two wings extending at equal both opposite angles relative to a slot of the cutting block, and the alignment rod includes a keyed portion, the keyed portion further including a key extending therefrom and a barrel having a rectangular cross-section, wherein the barrel and key have a width equal to widths of the wings and wherein opposite faces of the barrel and the key are separated by a distance equal to lengths of the wings.

In another aspect, a method of performing a resection includes fixing an anchor to a patient, positioning a cutting block into an intended position relative to the patient, the cutting block being connected to the anchor by a flexible linkage such that the cutting block has six degrees of freedom of motion relative to the anchor; and cutting bone through a cutting guide defined in the cutting block while the cutting block is in the intended position.

In some arrangements according to any of the foregoing, the method includes fixing the cutting block to the patient after the positioning step and before the cutting step.

In some arrangements according to any of the foregoing, the fixing step includes pushing spikes extending from the anchor into a portion of bone to be resected.

BRIEF DESCRIPTION OF THE DRAWINGS

FIG. 1 is an oblique perspective view of a resection guide coupled to a humerus according to an aspect of the disclosure.

FIGS. 2A-2F are oblique perspective views of various links of the resection guide of FIG. 1.

FIGS. 5A and 5B are oblique perspective views of an anchor according to a second arrangement.

FIGS. 9A and 9B are elevation views of a keyed portion of an alignment rod according to the resection guide of FIG. 7.

FIGS. 10A-10G are perspective views of links of a resection guide according to another arrangement.

FIG. 12A is a cross-sectional view of a portion of a link of a resection guide according to another arrangement.

FIG. 12B is a perspective view of a linkage according to the arrangement of FIG. 12A.

FIG. 12C is a cross-sectional view of a hinge within the linkage of FIG. 12B.

DETAILED DESCRIPTION

Figures 2A, 2B, 2C:
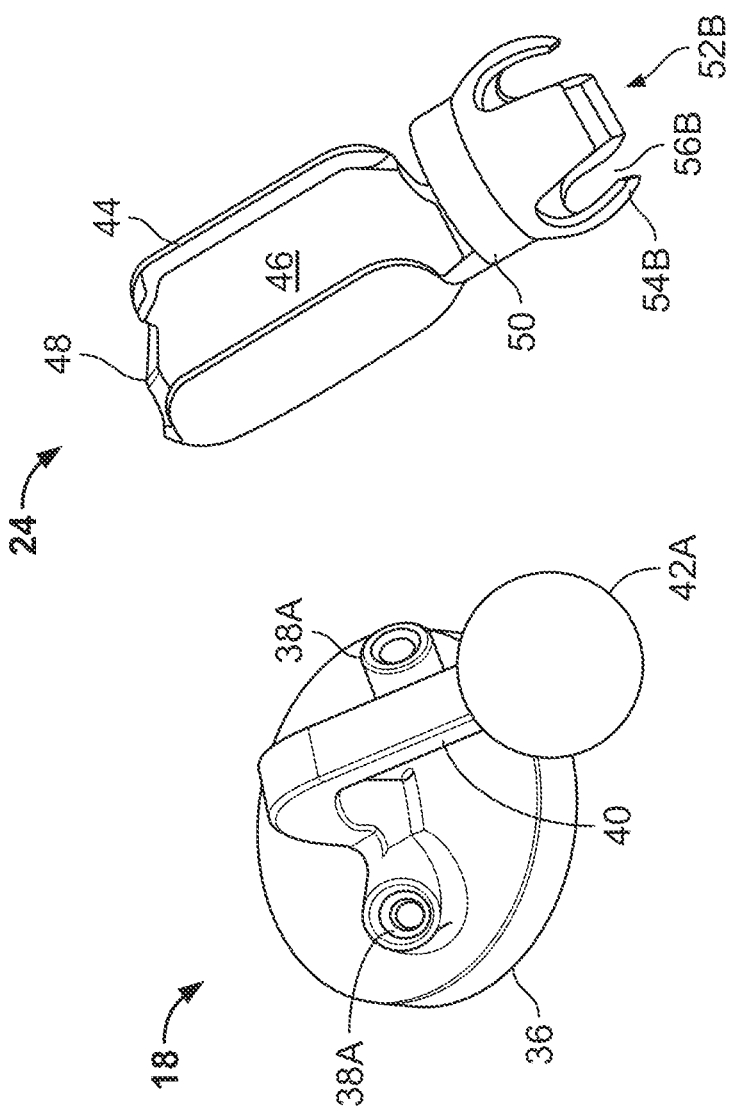

As used herein, the term "proximal," when used in connection with a surgical tool or device, or components of a device, refers to the end of the device closer to the user of the device when the device is being used as intended. On the other hand, the term "distal," when used in connection with a surgical tool or device, or components of a device, refers to the end of the device farther away from the user when the device is being used as intended. As used herein, the terms "substantially," "generally," "approximately," and "about" are intended to mean that slight deviations from absolute are included within the scope of the term so modified.

FIG. 1 illustrates a resection guide 10 mounted to a humeral head 12 of a humerus 14. Resection guide 10 includes a linkage 16 linking an anchor 18 to a cutting guide or cutting block 20. Anchor 18 is fixed to humeral head 12 with pins 22. Cutting block 20 is also fixed to humerus 14 near an anatomical neck of humerus 14 with pins 22. It should be understood that, although resection guide 10 is illustrated and described for use with a resection to the head 12 of a humerus 14, it may be used, with or without modifications, for resecting portions of other joints, such as the head of a femur.

Linkage 16 may include a plurality of interconnected rigid links of various types. The links of the illustrated arrangement include a slider link 24, two barbell links 26, a double socket link 28, and a cutting block link 30. Anchor 18 is slidably connected to slider link 24; a first barbell link 26 connects slider link 24 to a double socket link 28; a second barbell link 26 connects double socket link 28 to cutting block link 30; and cutting block link 30 connects to cutting block 20. Though linkage 16 of the illustrated arrangement includes various types of individual links, it is contemplated that linkage 16 according to other embodiments may be constructed from only a single type of link, such as a link including a ball and a socket connected by a bar.

Interconnection of the links in linkage 16 may provide linkage 16 with sufficient flexibility to give cutting block 20 six degrees of freedom relative to anchor 18 when anchor 18 is fixed to humeral head 12 but prior to fixing cutting block 20 to humeral head 12. An alignment rod 32 may extend from cutting block 20 to facilitate proper alignment of cutting block 20 with humerus 14. A user may orient cutting block 20 by aligning alignment rod 32 with the anatomical axis of humerus 14, before fixing cutting block 20 in place with pins 22. In addition or alternatively, alignment rod 32 may be used to verify desired positioning of cutting block 20 after cutting block 20 is fixed in place. The alignment rod 32 may also be used as a handle for manipulating or positioning the cutting block 20. Version rod connector 34 disposed at an end of alignment rod 32 has features, such as holes in the illustrated example, for retaining a version rod 35, which may be used as a reference to position the patient's forearm relative to cutting block 20.

FIGS. 2A-2F illustrate various elements of the resection guide 10 of FIG. 1. Shown in FIG. 2A, anchor 18 includes a base 36 which is illustrated as being generally circular or cylindrical, although other shapes may be appropriate. Base 36 may include two main opposing surfaces, including a bone-contacting surface and an opposite surface. The bone-contacting surface of base 36, although not shown in FIG. 2A, may include a contoured surface. The contoured surface may be concave or otherwise contoured to make better contact with the convex surface of humeral head 12. The surface of base 36 opposite the bone-contacting surface may be substantially flat. Base 36 may include one or more holes 38A to accommodate pins 22 for fixing anchor 18 to bone. In the illustrated embodiment, base 36 includes two holes 38A extending entirely through base 36 so that a pin 22 may pass completely through the holes 38A to fix the anchor 18 to the humerus 14. Further, in the illustrated embodiment, the two holes 38A define channels for accepting pins 22, the channels being positioned along non-parallel axes. However, in other embodiments, the anchor 18 may include more or fewer holes 38A at different positions and/or orientations than illustrated in FIG. 2A. Further, although holes 38A are illustrated as defining substantially cylindrical channels to receive pins 22 therethrough, the holes 38A may take other shapes to receive other fixation devices besides generally cylindrical pins. Post 40 may extend from the surface of base 36 opposite the bone-contacting surface. In the illustrated embodiment, post 40 includes a base portion extending substantially orthogonal to the surface of base 36 opposite the bone-contacting surface. The post 40 may also include a linking portion extending from the base portion in a direction substantially parallel to the surface of base 36 opposite the bone-contacting surface. The post 40 may further include a spherical member or ball 42A disposed at the free end of the linking portion of the post 40. Although post 40 shown in FIG. 2A includes a substantially right-angle bend, according to other arrangements, post 40 includes one or more bends at any suitable angle, or contains no bends and extends linearly to the ball 42A. As should be understood from the description herein, anchor 18 may serve as an anchor that couples to the humerus 14 and serves as a support or base for the rest of the resection guide 10.

As shown in FIG. 2B, slider link 24 may include an elongated sleeve 44 and a socket 52B. Sleeve 44 may have an arcuate cross-section extending across more than 90°. In the illustrated embodiment, sleeve 44 has a generally "C"-shaped or "U"-shaped cross-section. Sleeve 44 may further include a lip 48 at a first end of the sleeve 44, and socket stop 50 at a second end of the sleeve 44. Sleeve 44 may define a track 46 that is sized to tightly accommodate a spherical member or ball 42C of barbell link 26 (shown in FIG. 2C and described in greater detail below) so as to allow ball 42C to slide from lip 48 to socket stop 50 upon application of a sliding force, but to retain ball 42C in a stationary position within track 46 in the absence of an applied sliding force.

Still referring to FIG. 2B, the socket 52B of slider link 24 may be positioned on an opposite side of socket stop 50 from track 46. Socket 52B may be provided by flexible tabs 54B extending from a common base. Tabs 54B may each have a curved profile concave toward the other tabs 54B and thereby define a generally spherical space able to tightly accommodate ball 42C. Tabs 54B may be able to grip ball 42C because the spherical space within socket 52B may be more than half of a sphere. Stated another way, an arc centered on the center of the spherical space and defined between free ends of opposite tabs 54B subtends less than 180°. Notches 56B exist between tabs 54B to enable individual flexion of tabs 54B. It should be understood that, although socket 52B is described as receiving ball 42C, it may receive any other similar component therein, such as ball 42A of anchor 18.

Referring to FIG. 2C, barbell link 26 may include a bar 58 with a spherical member or ball 42C on each end. Bar 58 as illustrated in FIG. 2C as a straight cylinder, but in other arrangements bar 58 has one or more bends and/or cross-sectional shapes other than circular. Bar 58 preferably has a thickness or diameter less than a width of notches 56B, so that barbell link 26 may rotate more than 180° relative to a socket 52B while a ball 42C of barbell 26 is disposed within the socket 52B, as described above with regard to anchor 18 rotating relative to socket 52B of slider 24.

Notches 56 may enable a link having a ball 42C disposed within socket 52B to rotate at least 180° despite the extension of tabs 54B around more than half of the ball 42C). For example, notches 56B may be wider than a thickness of bar 58, so barbell link 26 may rotate across a range of more than 180° about socket 52B while barbell link's ball 42C is disposed within socket 52B with bar 58 travelling from disposition through one notch 56B to disposition through another, opposite notch 56B. Similar to track 46, the spherical space within socket 52B is sized to effectively grip ball 42C and to allow ball 42C to rotate within socket 52B when forced, but to hold ball 42C stationary relative to socket 52 in the absence of manipulation by a user. Socket 52B as described above may be attached to links other than slider link 24, and the foregoing description of socket 52B, tabs 54B, and notches 56B is generally true for sockets 52 included by other links described herein.

FIG. 2D illustrates double socket link 28. The double socket link 28 may include a cylindrical column 60 with a socket 52D on each end. Sockets 52D are generally alike to the socket 52D described above with regard to the slider link 24. Each socket 52D of double socket link 28 is thereby able to movably connect any link that has a ball, such as ball 42A of anchor 18 and ball(s) 42C of barbell links 26. As described above, any two links connected via the ball-and-socket joints of resection guide 10 may remain substantially stationary with respect to one another, for example via frictional engagement, in the absence of application of an intentional force to change the position of the two links connected via the ball-and-socket joint.

FIG. 2E illustrates cutting block connector 30. Cutting block connector 30 may include a socket 52E, cylindrical pillar 62 extending from socket 52E, and plug 64 extending from an end of pillar 62 opposite socket 52E. Plug 64, as illustrated, includes four elongate, flexible fingers 64*a*. Each finger 64*a* further includes a protrusion or rib 64*b* near an end of the finger 64*a* that is opposite from pillar 62. Ribs 64*b* cooperate with the flexibility of fingers 64*a* to enable plug 64 to lock into certain receiving features, described in greater detail below. Such locking may be reversible or irreversible depending on details such as sharpness of edges of ribs 64*b*, resilience of fingers 64*a*, and geometry of the receiving features. For example, plug 64 may reversibly lock into a cylindrical opening in a surface having detents or a larger cavity recessed from the surface if a collective diameter of the ribs is greater than the diameter of the cylindrical opening, as the resilience of the fingers 64*a* will push the ribs 64*b* outward into engagement with the detents or cavity. Plug 64 as illustrated includes four fingers 64*b*, but any number of fingers 64*a* greater than one, or one compressible finger 64*a*, may operate as described above. In other arrangements, the plug 64 includes two or more fingers 64*a*. In still further arrangements, plug 64 includes other features for reversible or irreversible locking engagement with corresponding receiving features.

FIG. 2F illustrates cutting block 20. Cutting block 20 includes holes 38F in a quantity and orientation sufficient for fixing cutting block 20 to bone with pins 22. In the illustrated embodiment, cutting block 20 includes two holes 38F that each define substantially cylindrical channels extending through opposing surfaces of the cutting block 20. The channels defined by the holes 38F are also illustrated as having non-parallel axes, similar to the holes 38F of anchor 18. However, as with the holes 38A of anchor 18, cutting block 20 may include more or fewer holes 38F, and those holes 38F may have different shapes and define channels having shapes to receive fixation members therein, whether the fixation members are substantially cylindrical pins 22 or differently shaped fixation members. Cutting block 20 includes a cutting guide in the form of a slot 66 extending along a lengthwise direction of cutting block 20. Slot 66 extends through a thickness of cutting block 20 defined from a proximal side of cutting block 20 to a distal side of cutting block 20, but is otherwise enclosed by cutting block 20 on all sides. However, in some embodiments, the slot 66 may only be enclosed on one side. Cutting block 20 further includes an aperture 68 for engagement with alignment rod 32. Aperture 68 includes cylinder 68*a* and two channels 68*b* extending along cylinder 68*a*. Each channel 68*b* may extend from cylinder 68*a* at an equal, but opposite, angle relative to slot 66. Cutting block 20 still further includes a recess 70 at each lateral end (only one recess 70 visible from the perspective of FIG. 2F). Recesses 70 are shaped for engagement with plug 64. Recesses 70 of the illustrated embodiment include a cylindrical opening in cutting block 20 with a diameter less than a collective diameter of ribs 64*b*. The resilience of fingers 64*a* therefor forces ribs 64*b* against the surface of recess 70 when plug 64 is inserted in recess 70 to create frictional engagement and retention of plug 24 within recess 70. Further, detents or a cavity may be located within recess 70 for receiving the ribs 64*b* as described above with regard to FIG. 2E. Engagement of plug 64 with recess 70 enables connection of cutting block 20 to cutting block connector 30 as shown in FIG. 1, which in enables pivotal connection of cutting block 20 to a barbell 26 or any ball 42.

Figure 3A:
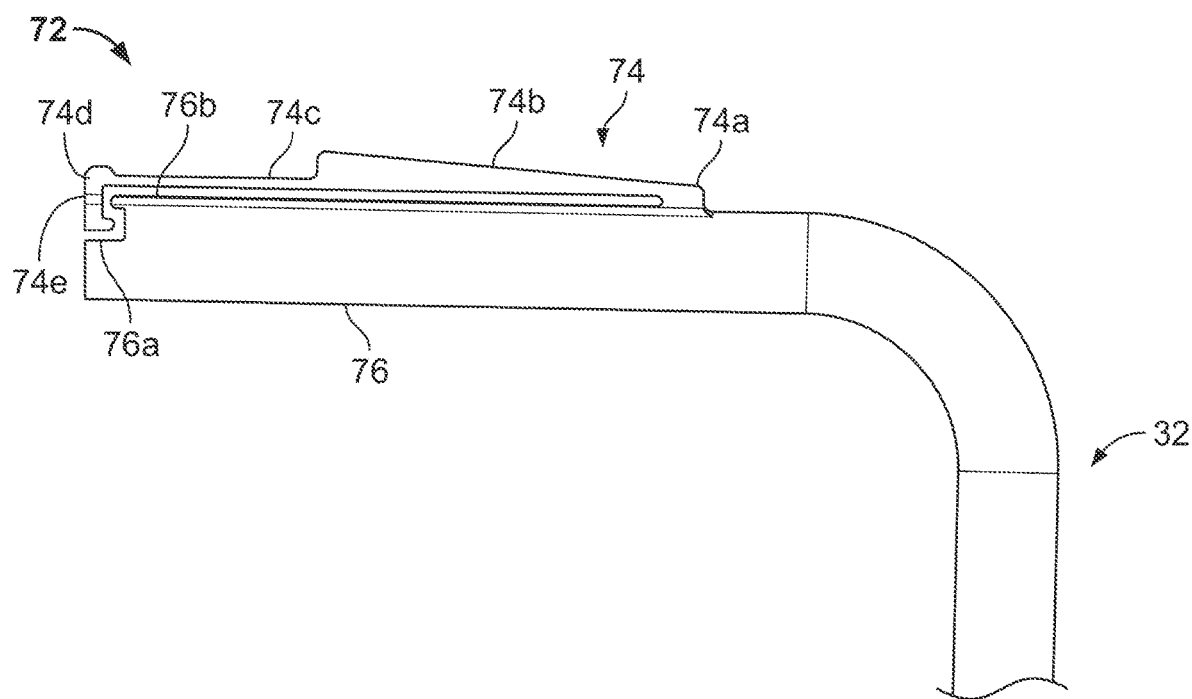
FIGS. 3A and 3B are elevation views of a keyed portion of an alignment rod according to an arrangement.
Figure 3B:
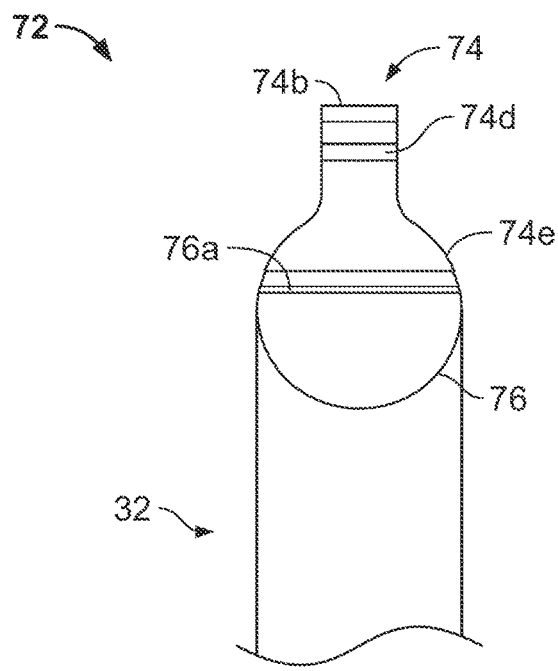

Turning to FIGS. 3A and 3B, alignment rod 32 includes keyed portion 72. Keyed portion 72 includes a key 74 connected to and extending substantially parallel to a barrel 76, which extends substantially perpendicular to a length of alignment rod 32. Key 74 is flexibly connected to barrel 76 at connection point 74*a*, and extends substantially parallel to barrel 76 away from a longitudinal portion of alignment rod 32. Ramp surface 74*b* of key 74 extends away from barrel 76 with increasing distance from connection point 74*a*. The resulting ramped profile of key 74 may be helpful for operating key 74, such as by using a thumb or finger to press key 74 against barrel 76. Valley 74*c* extends between ramped surface 74*b* and tooth 74*d* located at a far end of key 74 from connection point 74*a*. An outer surface of valley 74*c* is closer to barrel 76 than ramped surface 74*b* and an extremity of tooth 74*d*.

Barrel 76 is sized to closely fit within cylinder 68*a*, and a height of valley 74*c* away from barrel 76 is approximately equal to a height of channels 68*b* away from cylinder 68*a*. A highest point of ramped surface 74*b* is immediately adjacent valley 74*c* and has a height greater than the height of the channels 68*b*. No height transition is provided between the highest point of ramped surface 74*b* and valley 74*c* or between tooth 74*d* and valley 74*c*.

Key 74 is engageable with aperture 68 via insertion of barrel 76 into cylinder 68*a* and insertion of key 74 into either channel 68*b*. Key's 74 flexibility and height profile enables it to lock into aperture 68. Key 74 may deflect such that tooth may enter either channel 68*b* while barrel 76 enters cylinder 68*a*. In other words, as the leading end of key 74 begins to pass through cylinder 68*a*, the key may flex to bring the bottom surface of the key 74 (as viewed in FIG. 3) closer to an adjacent surface of barrel 76. When key 74 is advanced through aperture 68 far enough that tooth 74d exits aperture 68 on an opposite side of cutting block 20 from alignment rod 32, key 74 snaps back toward key's 74 undeflected shape to lock key 74 into place in channel 68b. The lack of transition between either the highest point of ramp 74b or tooth 74d and valley 74c prevents key 74 from unintentionally being withdrawn back though aperture 68 or sliding entirely through aperture 68. Valley 74c may have a width equal to or slightly exceeding a length of aperture 68 through cutting block 20 to substantially eliminate sliding of keyed portion 72 within aperture 68 when key 74 is locked into place in channel 68b. To remove key 74 from aperture 68, a surgeon may manually depress key 74 by applying pressure to ramped surface 74b to deflect the key 74 such that tooth 74d may fit within channel 68b before withdrawing key 74.

An engaged orientation of the alignment rod 32 relative to cutting block 20 depends on which channel 68b key 74 is inserted through. Because each channel 68b extends from cylinder 68a at an equal but opposite angle relative to slot 66, cutting block 20 may be used with either a patient's left shoulder or right shoulder if alignment rod 32 is keyed to the appropriate channel 68b.

In the illustrated example, key 74 further includes a hook 74e extending toward a central axis of barrel 76 away from an end of key 74 furthest from connection point 74a. Barrel 76 may include an indentation 76a to accommodate hook 74e. Hook 74e may hook back toward connection point 74a, and indentation 76a may include a lip 76b. Lip 76b may extend into indentation 76a beyond an extremity of hook 74e. Lip 76b thereby prevents key 74 from being bent far enough away from barrel 76 to break key 74.

Figure 4B:
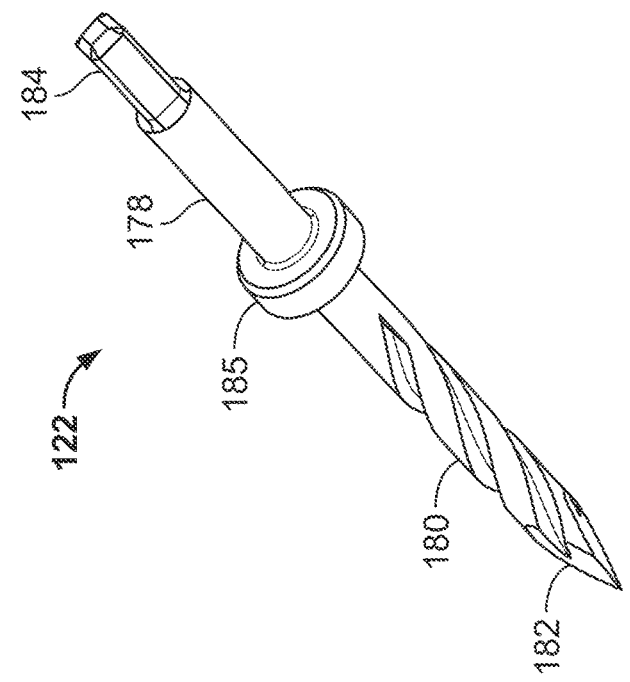
FIG. 4B is an oblique perspective view of a pin according to a second arrangement.
Figure 4A:
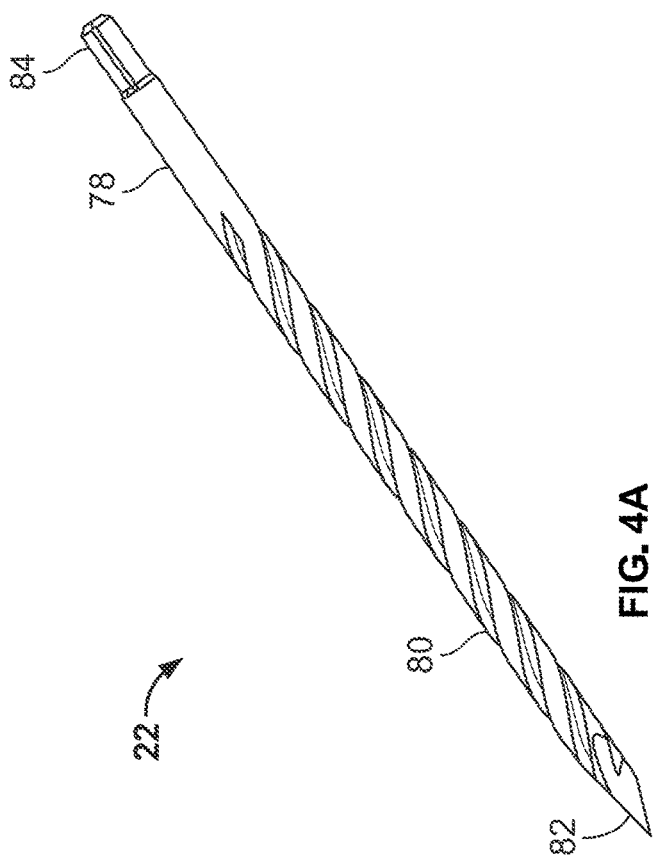
FIG. 4A is an oblique perspective view of a pin according to a first arrangement.

FIG. 4A illustrates pin 22 as may be used to fix links to bone. Pin 22 includes an unfluted portion 78, a fluted shank 80 distal of unfluted portion 78, and a point 82 at a distal end of fluted shank 80. A drivable element 84 is located at a proximal end of unfluted portion 78. In the illustrated example, polygonal drivable element 84 is a polygonal shaft, specifically a shaft with a square cross section. However, drivable element 84 may be a shaft of any other polygonal cross section, or any other drivable feature, such as a Phillips or flat screw head.

FIG. 4B illustrates a pin 122 according to another arrangement. Pin 122 includes a polygonal drivable element 184, unfluted portion 178, fluted shank 180, and point 182, listed from proximal to distal, generally as described with regard to pin 22 of FIG. 4A. Pin 122 further includes collar 185 extending radially outward from unfluted portion 178 and having a larger diameter than holes 38 in anchor 18 or cutting block 20. Collar 185 thereby limits travel of pin 122 through any hole 38 to prevent pin 122 from interfering with the cutting tool. According to some arrangements, pin 122 of FIG. 4B is used to fix cutting block 20 and anchor 18 to bone. According to further arrangements, pin 122 of FIG. 4B is used to fix anchor 18, and pin 22 of FIG. 4A is used to fix cutting block 20.

Figure 4C:
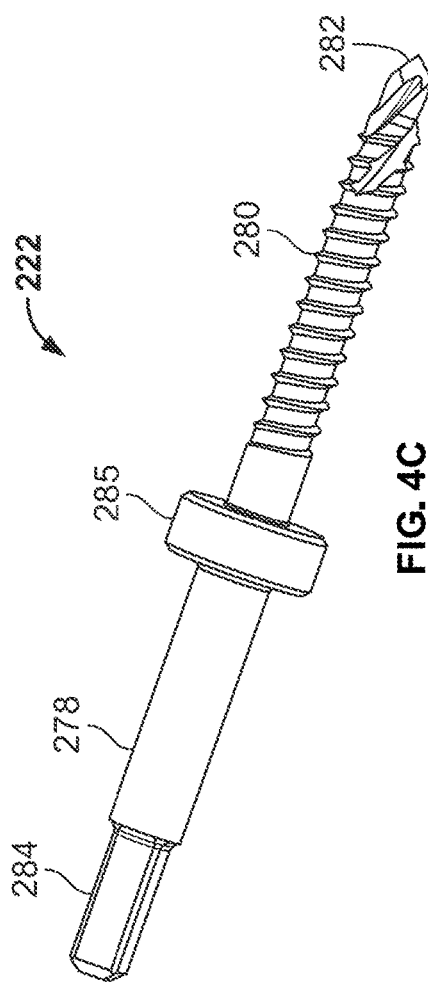
FIG. 4C is an oblique perspective view of a pin according to a third arrangement.

FIG. 4C illustrates a pin 222 according to another arrangement. Pin 222 includes a polygonal drivable element 284, unthreaded portion 278, collar 285, threaded shank 280, and point 282, listed from proximal to distal, generally as described with regard to pin 122 of FIG. 4B. Point 282 alone is fluted to assist in entry to bone. Threading on threaded shank 280 is pitched to be self-tapping Though pin 222 is illustrated with single start threading, alternative arrangements of threaded shank 280 may be double start threaded or more, and individual threads may have different heights.

Each of the above described pins 22, 122, 222 has certain advantages and can be used where appropriate and according to a surgeon's preference with any other aspect of the present disclosure.

FIGS. 5A and 5B illustrate an anchor 118 according to another arrangement. Anchor 118 includes spikes 138 extending from base 136. Spikes 138 enable anchor 118 to be fixed to the patient by pressing spikes 138 into humeral head 12. Although not shown in connection with anchor 18, anchor 18 may include spikes similar to spikes 138. Further, engagement features other than the spikes shown may be suitable for use with anchor 18 or anchor 118. Though anchor 118 is illustrated without pinholes, anchor 118 may include both spikes 138 and pinholes similar to the pinholes described and shown in connection with anchor 18. Similar to anchor 18, anchor 118 includes post 140 extending from a planar surface of base 136 with ball 142A disposed at an end of post 140 opposite from base 136. In contrast to post 40, post 140 as shown in FIGS. 5A and 5B is a straight cylinder, including no right angle bend. However, straight or bent posts may be used interchangeably with various arrangements of anchor 118 as appropriate for an operation. The option of a straight or angled post can provide additional clearance if correctly chosen for a given surgery, which can be beneficial for surgeries performed within tight spaces. Also, as with anchor 18, the base 136 of anchor 118 may include a bone-contacting surface 136a having a contoured surface, such as a concave surface, which may help make better contact with the convex surface of humeral head 12.

Figure 6:
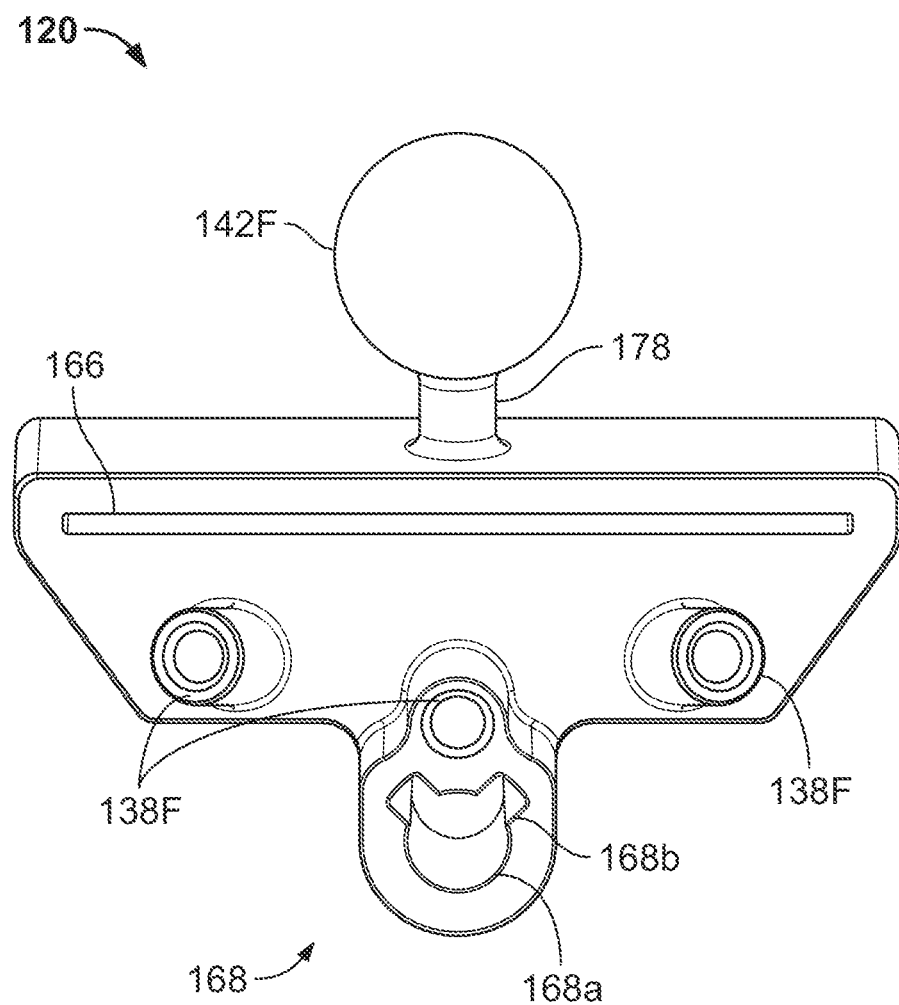
FIG. 6 is an oblique perspective view of a cutting block according to a second arrangement.

FIG. 6 illustrates a cutting block 120 according to another arrangement. Cutting block 120 is generally similar to cutting block 20 of FIG. 2F, with notable differences including that cutting block 120 includes post 178 extending from block 120 with ball 142F disposed at an end of post 178. Post 178 and ball 142F enable pivotable connection of cutting block 120 to any other link including a socket similar to those described above. Pinholes 138F, slot 166, and aperture 168, which includes cylinder 168a and channels 168b, are generally similar to pinholes 38F, slot 66, aperture 68, cylinder 68a, and channels 68b of FIG. 2F, and are thus not described in greater detail herein.

Figure 7:
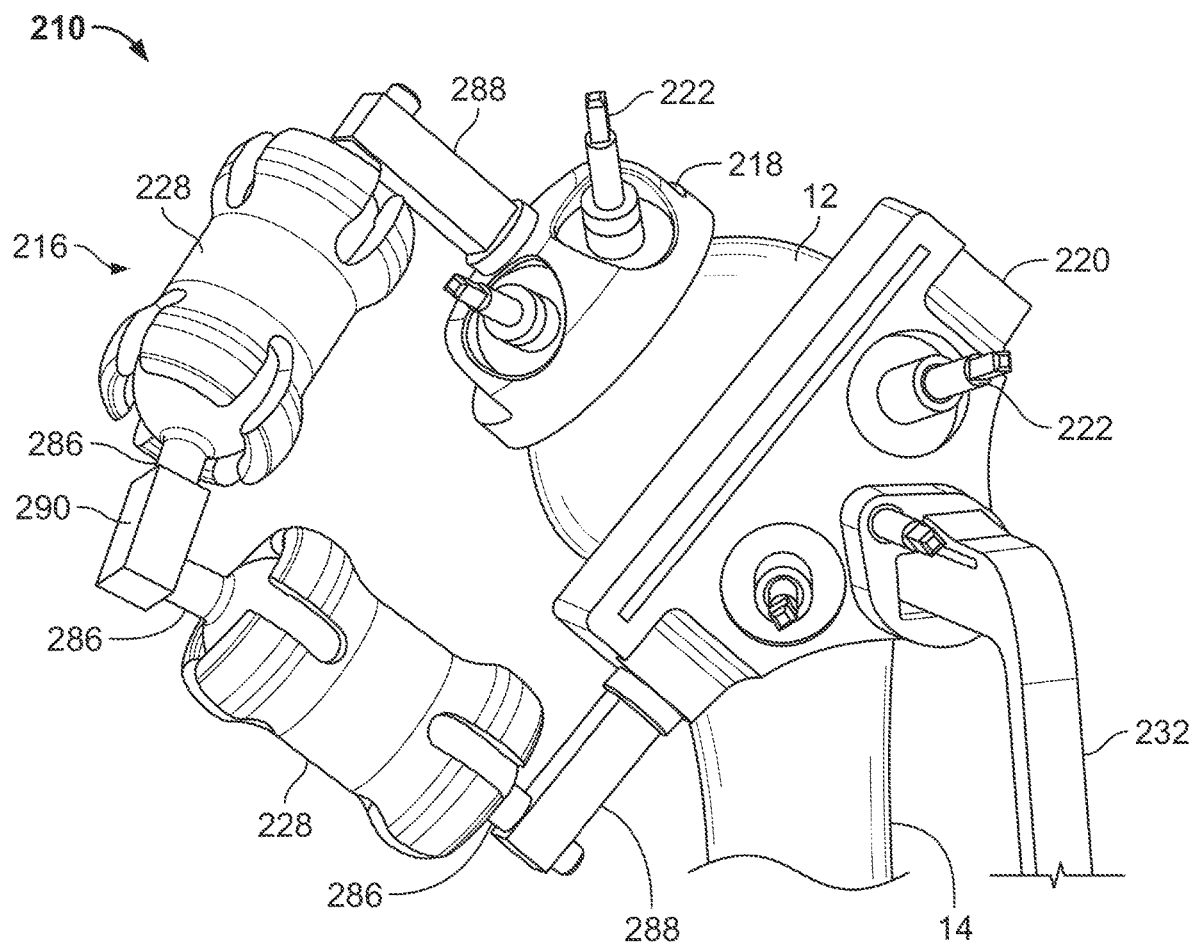
FIG. 7 is an oblique perspective view of a resection guide coupled to a humerus according to another arrangement.

FIG. 7 illustrates a resection guide 210 according to another arrangement mounted to humeral head 12 of humerus 14. Resection guide 210 includes a linkage 216 linking an anchor 218 to a cutting guide or cutting block 220 and providing six degrees of freedom of motion therebetween in a manner similar to the resection guide 10 and linkage 16 illustrated in FIG. 1. Anchor 218 and cutting block 220 are respectively fixed to humerus 14 at humeral head 12 and near an anatomical neck of humerus 14 with pins 222 in generally the same manner as resection guide 10 of FIG. 1. It should be understood that, although resection guide 210 is illustrated and described for use with a resection to the head 12 of a humerus 14, it may be used, with or without modifications, for resecting portions of other joints, such as the head of a femur.

The illustrated arrangement includes two double socket links 228, with a ball module 286 pivotably disposed in each socket of both double socket links 228. Anchor 218 and cutting block 220 both have a plug module 288 engaged therein, with ball modules 286 pivotably connecting each plug module 288 to a double socket link 228. Similarly, an elbow module 290 is pivotably connected to both double socket links 228 by two ball modules 286. Pins 222, which may be replaced with either pin 22 of FIG. 4A or pin 122 of FIG. 4B, fix anchor 218 to the head 12 of humerus 14, and fix cutting block 220 to humerus 14 near an anatomical neck of humerus 14.

Figure 8C:
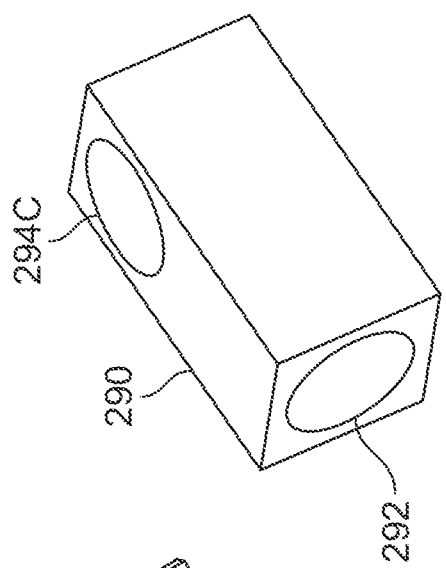
FIGS. 8A-8E are oblique perspective views of various links of the resection guide of FIG. 7.
Figure 8B:
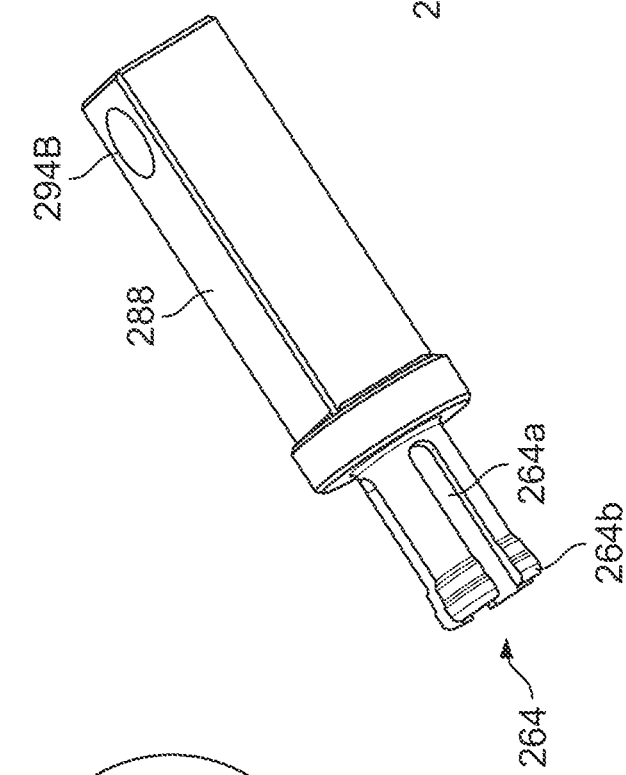
Figure 8A:
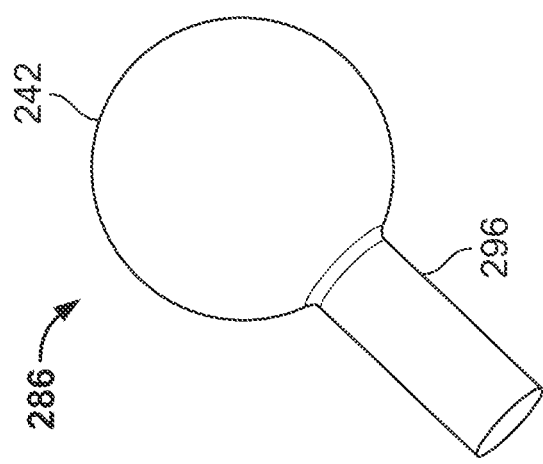

Ball module 286 shown in FIG. 8A includes a ball 242 and a peg 296 extending from ball 242. Plug module 288 shown in FIG. 8B includes a through bore 294B sized and shaped to engage with peg 296 of ball module 286. Plug module 288 further includes a plug 264 extending perpendicular to through bore 294B and having fingers 264a and ribs 264b generally similar to the plug 64 described with regard to FIG. 2E. Engagement of peg 296 into through bore 294B enables pivotable connection of plug 264, and by extension any other link having a recess that plug 264 may engage, such as recesses 270D and 270E described below, to a socket with an offset and ninety degree angle. Elbow module 290 illustrated in FIG. 8C includes a through bore 294C and a blind bore 292 extending perpendicular to through bore 294C. Through bore 294C and blind bore 292 are similarly sized and shaped to engage with peg 296. Elbow module 290 may therefore connect two ball modules 242 extending at a right angle relative to one another.

As illustrated, peg 296, through bores 294B and 294C, and blind bore 292 are all cylindrical in shape. However, peg 296 and bores 294B, 294C, and 292 may have any other cross-sectional shape that would enable peg 296 to engage with bores 294B, 294C, and 292 such that peg 296 may not slide or rotate within bores 294B, 294C, or 292 without force applied by a user. In any shape, peg 296 may have a slight interference fit with bores 294B, 294C, or 292 to inhibit unintended motion of peg 296 relative to bores 294B, 294C, or 292.

Figure 8E:
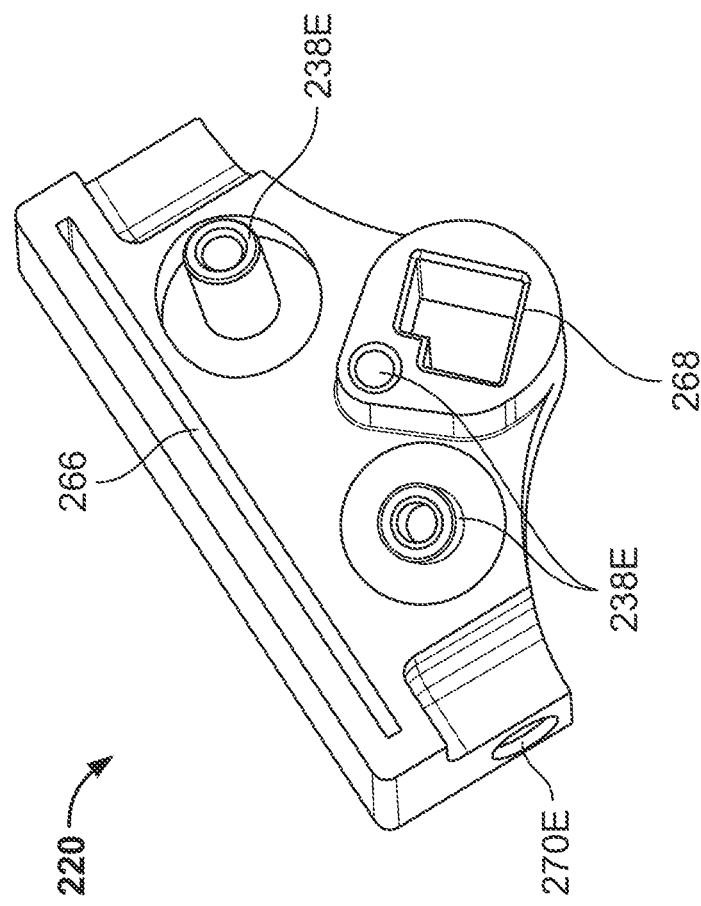
Figure 8D:
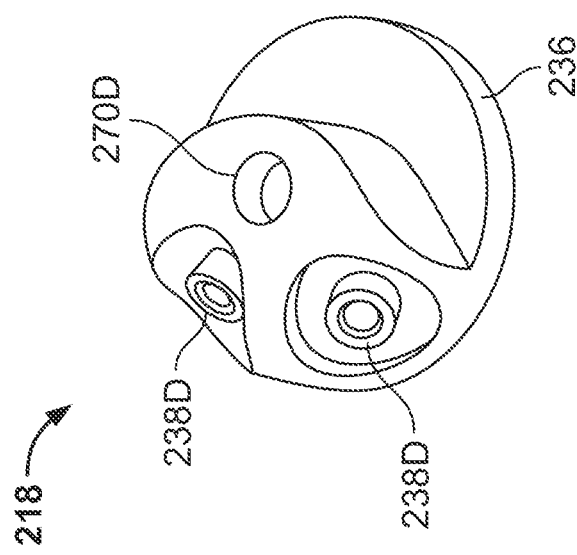

Anchor 218 as illustrated in FIG. 8D includes a base 236 and pinholes 238D generally similar to those described above with regard to anchor 18 illustrated in FIG. 2A. Anchor 218 further includes a recess 270D generally similar to the recess described above in connection with the cutting block 20 illustrated in FIG. 2F. Anchor 218 may thereby engage a plug, such as plug 264 of plug module 288 or plug 64 of cutting block connector 30. Though not illustrated, a reverse side of base 236 may include one or more spikes for seating base 236 to bone before any pins are placed through pinholes 238D.

FIG. 8E illustrates a cutting block 220. Cutting block 220 is generally similar to cutting block 20 of FIG. 2F, with notable differences including that cutting block 220 includes a symmetrical V-shaped aperture 268. The V-shape includes two wings extending at equal, but opposite, directions relative to slot 266. Pinholes 238E, slot 266, and recess 270E, are generally similar to pinholes 38F, slot 66, and recess 70 of FIG. 2F, and are thus not described in greater detail herein.

Turning to FIGS. 9A and 9B, alignment rod 232 includes keyed portion 272. Keyed portion 272 includes a barrel 276 and key 274 having a rectangular cross-section of equal width to both wings of the symmetrical V-shape of aperture 268. Key 274 connects to barrel 276 at a connection point 274a where barrel 276 transitions from a height equal to lengths of the two wings of the symmetrical V-shape of aperture 268 to a lesser height, and key 274 extends parallel to barrel 276 from connection point 274a to an end of barrel 276. Barrel 276 has a rectangular cross section along its length in contrast to the round barrel 76 illustrated in FIGS. 3A and 3B. A distance between opposite faces of barrel 276 and a valley 274c of barrel 274 is equal to the lengths of the two wings of the symmetrical V-shape of aperture 268, meaning that the keyed portion 272 can fit into aperture 268 in one of two positions with little or no room to move relative to cutting block 220. Ramped surface 274b, tooth 274d, hook 274e, indentation 276a, and lip 276b are generally similar to ramped surface 74b, tooth 74d, hook 74e, indentation 76a, and lip 76b of FIGS. 3A and 3B, and are thus not described in greater detail herein.

Figure 10A:
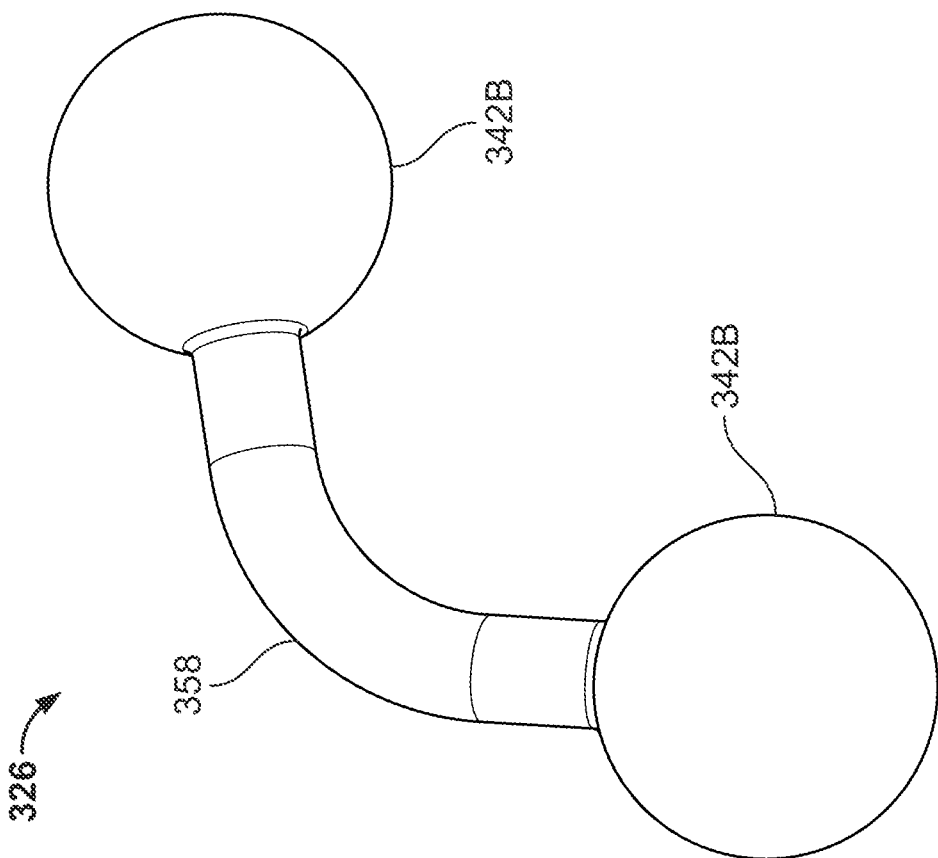

Another group of links is shown in FIGS. 10A-10F. The links include an anchor 318 as shown in FIG. 10A, having a post 340 ending in a ball 342A and extending from a base 336. Anchor 318 is generally similar to the anchors as described above, such as anchor 18, except that anchor 318 includes four fixation holes 338A in base 336.

Figure 10B:
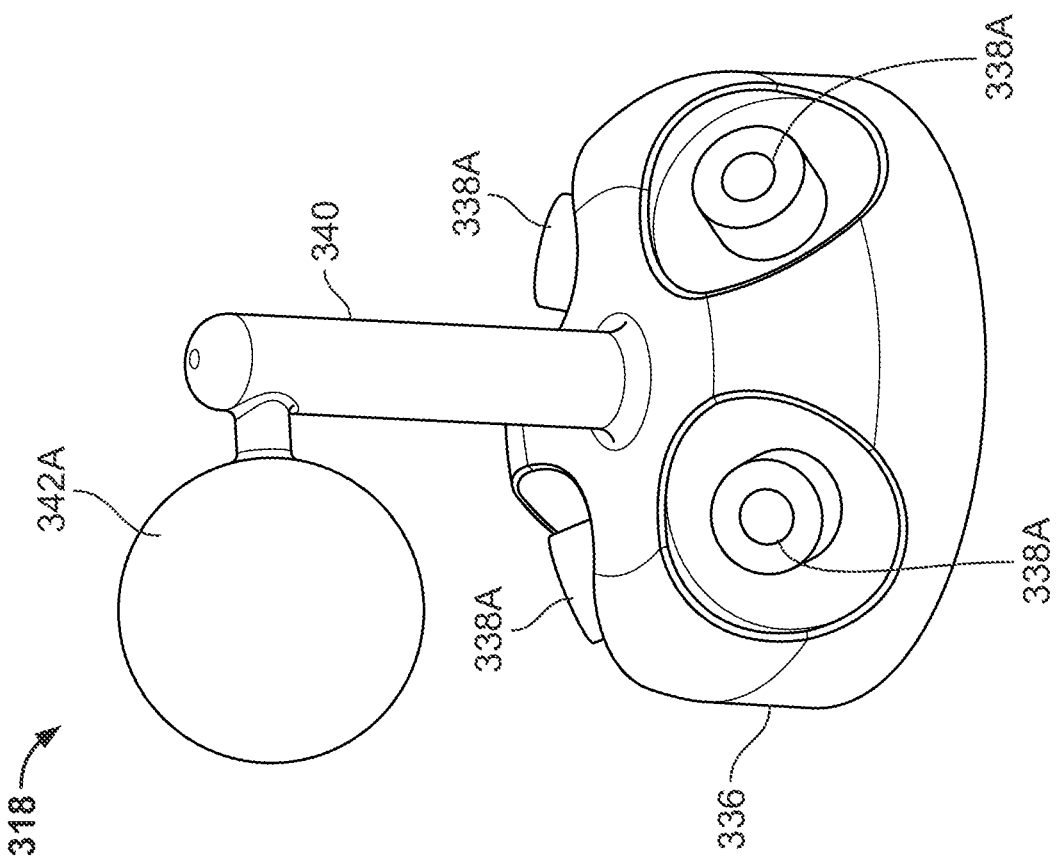
Figure 10D:
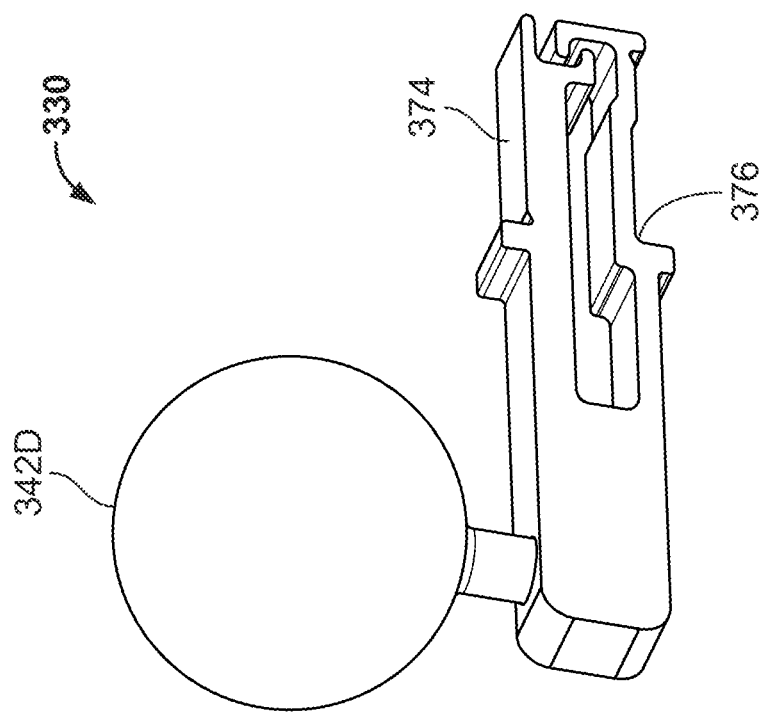

As shown in FIG. 10B, a non-linear barbell 326 includes an arcuate bar 358 with a ball 342B on either end. Bar 358 can be an arc subtending any angle, or any other non-linear shape.

Figure 10C:
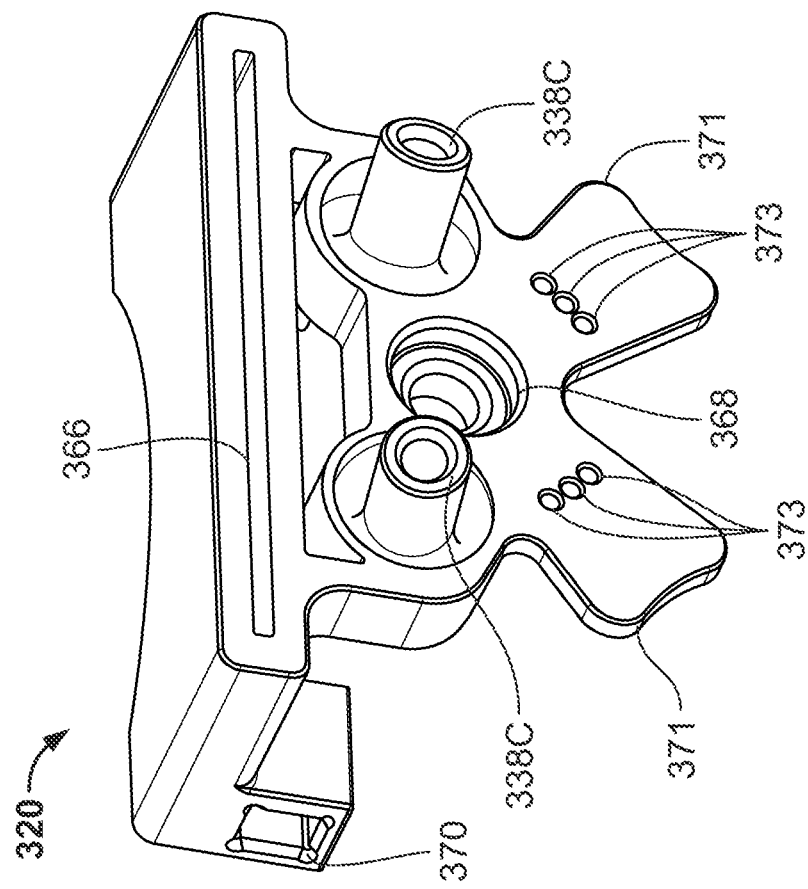

Turning to FIG. 10C, a cutting block 320 has a cutting slot 366 and fixation holes 338C generally similar to above described cutting blocks 20, 120, 220. Cutting block 320 also includes two recesses 370 (only one being visible from the perspective of FIG. 10C). Recesses 370 are generally square in cross section in the illustrated example and are configured with an internal ridge or ledge for engagement by two key arms 374, 376 of a cutting block link 330 shown in FIG. 10D. Key arms 374, 376 function generally alike to keyed portion 272 of alignment rod 232 as described above. Cutting block link 330 of the illustrated example also includes a ball 342D, but in alternative arrangements may instead or in addition include a socket.

Returning to FIG. 10C, cutting block 320 also includes an aperture 368. Aperture 368 of the illustrated example is circular in cross-section, lacking the channels 68a, 68b or other aligning features illustrated and described above with regard to the apertures of other cutting blocks. Cutting block 320 instead includes two projections 371 extending away from aperture 368 at symmetrical opposite angles corresponding to appropriate alignment angles for a patient's left or right arm. Each projection 371 includes three index holes 373. In other examples, each projection 371 could include more or fewer index holes 373.

Turning to FIG. 10E, a short alignment bar 332E is fastened to cutting block 320 by a fastener 375, such as a thumb screw, extending through short alignment bar 332E into engagement with aperture 368. Short alignment bar 332E ends in a version rod connector 334E. A back surface of short alignment bar 332E shown in FIG. 10F includes a boss 377 for engaging any one of the index holes 373. Boss 377 is spaced from a hole in short alignment bar 332E for accepting fastener 375 by a distance matching a distance between aperture 368 and index holes 373. Short alignment bar 332E can therefore be set to one of three angles within a range provided by either projection 371 by placing boss 377 into an index hole 373 and fastening short alignment bar 332E in place with fastener 375.

Figure 10G:
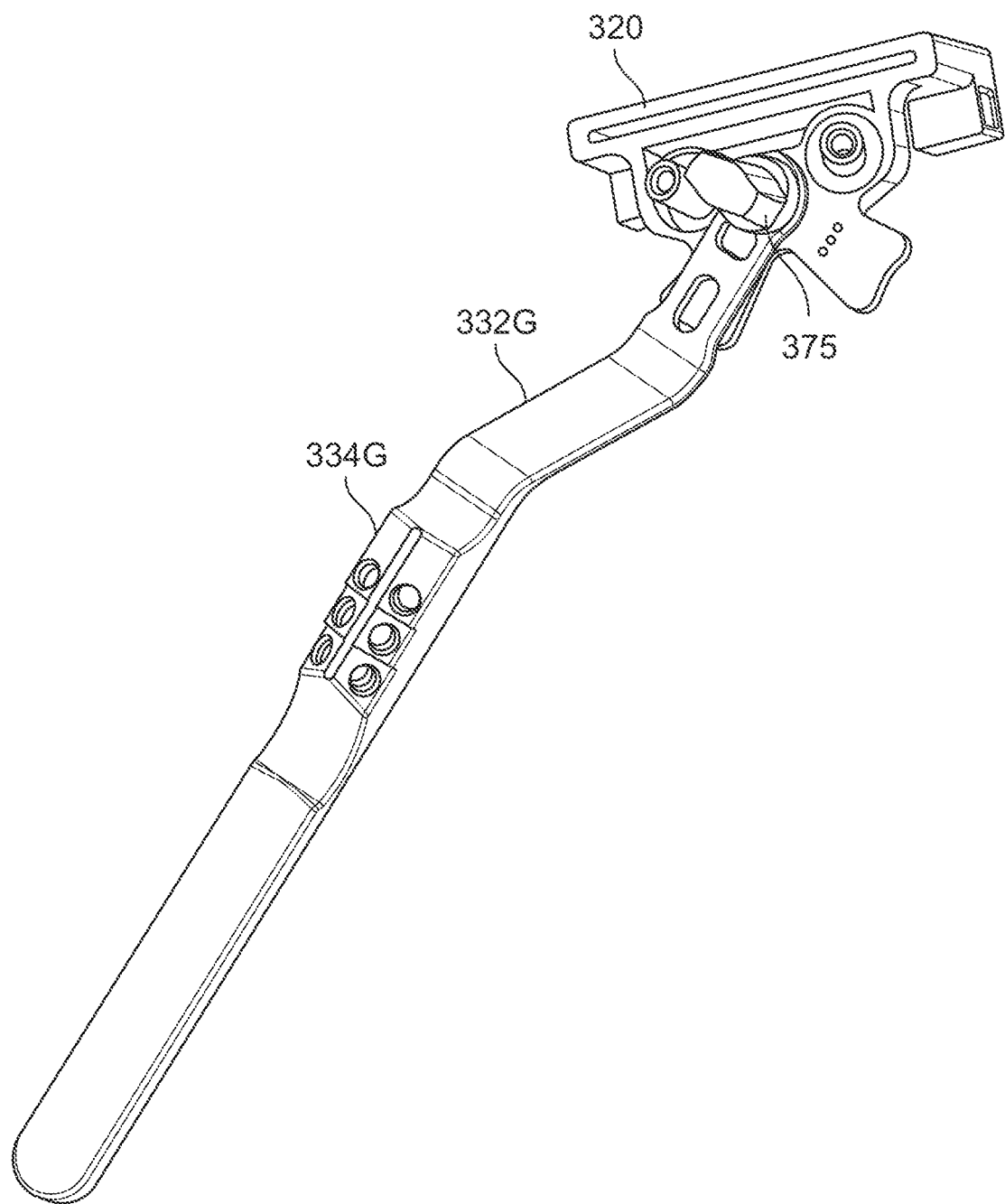

FIG. 10G shows a long alignment bar 332G, also including a version rod connector 334G near a midpoint thereof. A back surface of long alignment bar 332G includes a boss generally alike to boss 377 of short alignment bar 332E such that long alignment bar 332G can also be fastened to any of six alignments provided by index holes 373.

Figure 11B:
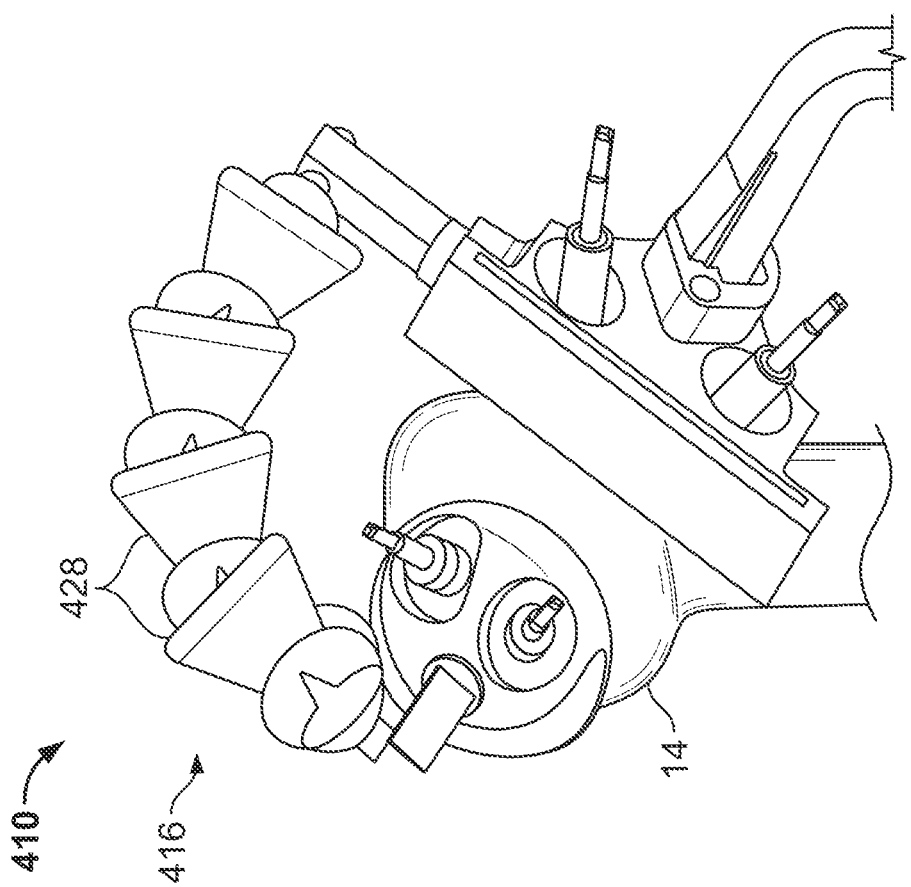
FIG. 11B is a perspective view of a resection guide including links according to FIG. 11A.
Figure 11A:
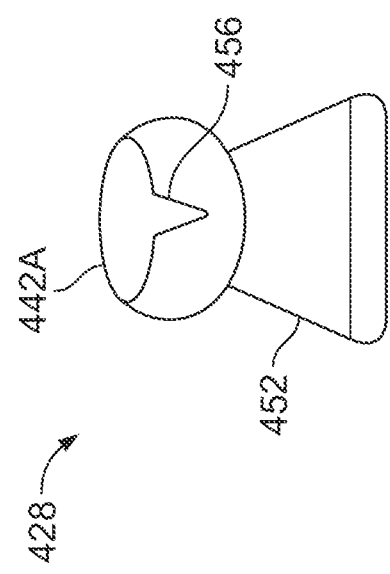
FIG. 11A is a perspective view of a link of a resection guide according to another arrangement.

FIG. 11A illustrates a repeatable link 428. Repeatable link 428 includes a bowl 442A and a hollow cone 452 defining a roughly spherical socket (not illustrated). Bowl 442A includes a notch 456 providing bowl 442A with some flexibility to expand or contract. As shown in FIG. 11B, bowl 442A can therefore expand to act as a socket on a ball of any of the links described elsewhere in this disclosure or be compressed to act as a ball within a socket of any link, including the socket defined within cone 452 of another repeatable link 428. Several repeatable links 428 can therefore be linked directly to one another in a chain 416 or repeating linkage to provide a flexible cutting guide 410.

Figure 11D:
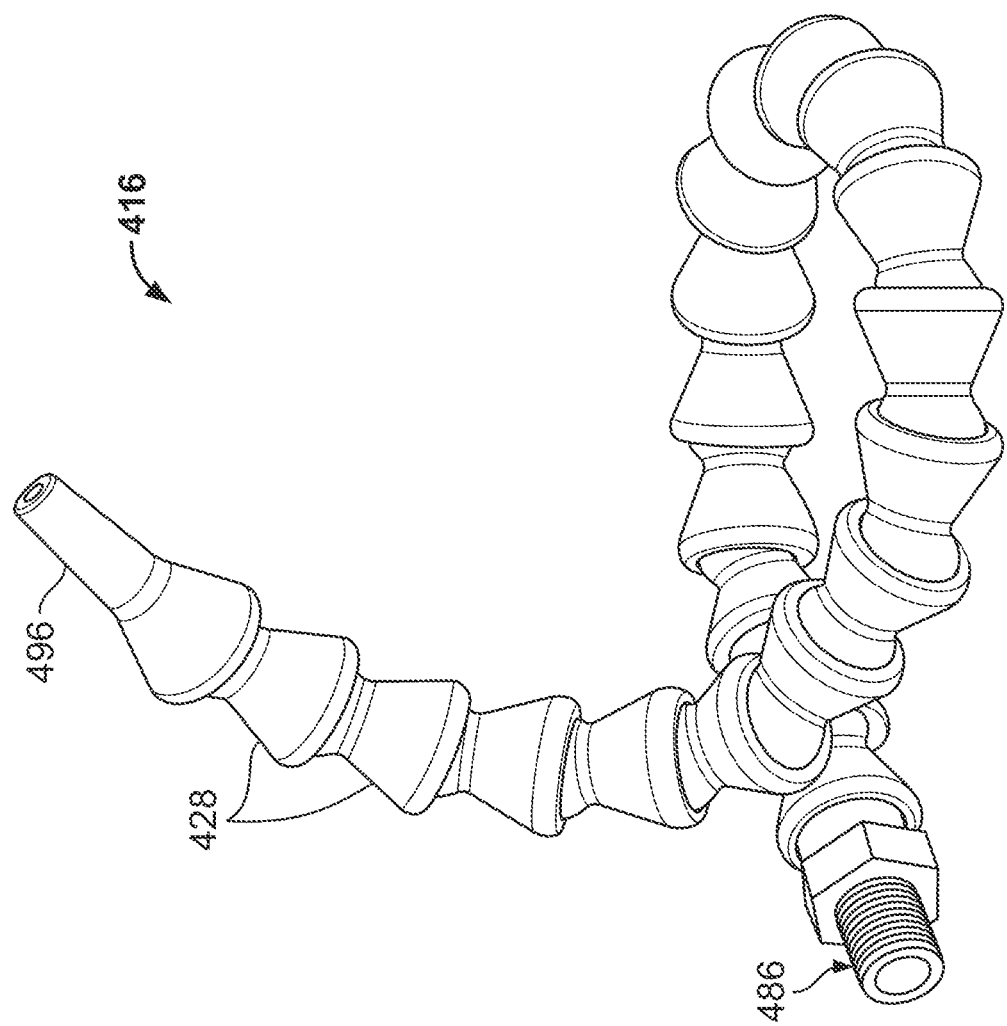
FIG. 11D is a perspective view of a resection guide including the links of FIGS. 11A and 11C.
Figure 11C:
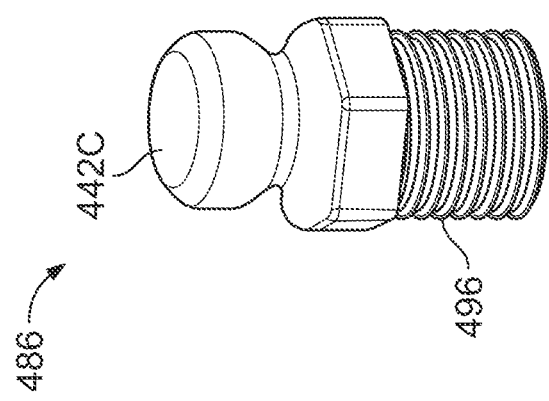
FIG. 11C is a perspective view of another link according to the arrangement of FIGS. 11A and 11B.

FIG. 11C shows a threaded link 486. Threaded link 486 includes a helically threaded base 496 and a bowl 442C similar to bowl 442A of repeatable link 428. Bowl 442C can similarly act as a ball within a socket defined within cone 452 of a repeatable link 428, threaded base 496 of threaded link 486 can provide an end of a chain 416 as shown in FIG. 11D. At an opposite end of chain 416 as shown in FIG. 11D is taper link 496, which may press fit into holes or apertures of other links, such as a hole in a side of any of the cutting blocks described in this disclosure, enabling the chain 416 of FIG. 11D to be used as a positionable cutting guide in another manner.

FIG. 12A illustrates a flexible link 529. Flexible link 529 includes four flexible leaves 531 extending from an externally threaded stem 533, though alternative arrangements including any number of leaves 531 greater than or equal to two are contemplated. Leaves 531 collectively form a generally spherical socket for accepting a ball 42 of any link according to the present disclosure. Adjacent leaves 531 (or portions thereof) may be separated by slots or other recesses to enhance the flexibility of the leaves. An internally threaded sleeve 535 is threaded onto externally threaded stem 533 and extends partially over leaves 531. Thus, sleeve 535 can be advanced or withdrawn along leaves 531 to adjust a tightness of the socket provided thereby and to adjust leaves' 531 freedom to bend outward, with tightness of the socket increasing and freedom of leaves 531 decreasing as sleeve 535 is advanced further along leaves 531. As the socket is tightened onto ball 42, friction impeding rotation of ball 42 within socket also increases.

Figure 13B:
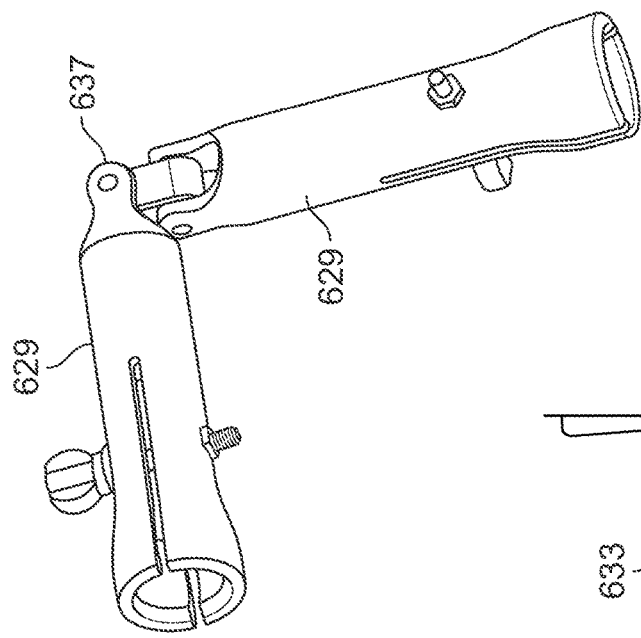
FIG. 13B is a cross-sectional view of a linkage according to the arrangement of FIG. 13A.
Figure 13C:
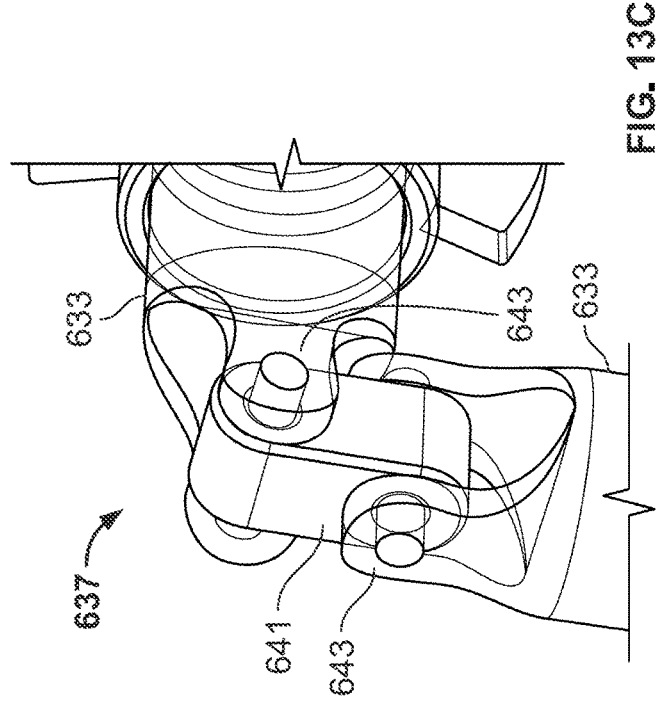
FIG. 13C is a perspective view of a hinge within the linkage of FIG. 13B.
Figure 13A:
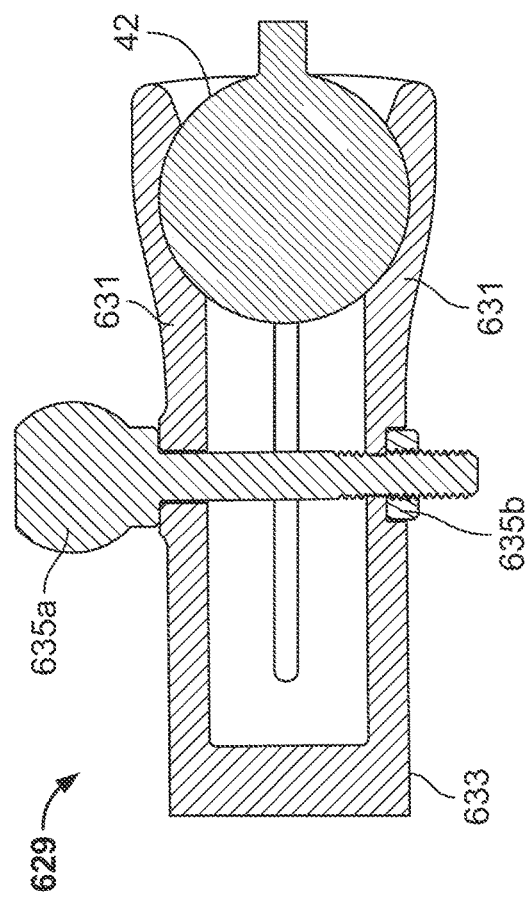
FIG. 13A is a cross-sectional view of a portion of a link of a resection guide according to another arrangement.

Turning to FIG. 12B, two flexible links 529 are joined together at a joint 537. As shown in FIG. 12C, joint 537 is provided at an overlap between two tabs 539, each tab extending from a respective stem 533 of a respective one of the flexible links 529. Both tabs 539 include an internally threaded hole extending therethrough, and a joint screw 541 extends through both internally threaded holes. Joint screw 541 includes an unthreaded neck 541a, disposed within a first of the two internally threaded holes, and an externally threaded base 541b threadingly engaged with a second of the two internally threaded holes. Both tabs 539 can therefore be tightened or loosened against a head of joint screw 541 by rotating joint screw 541, and particularly by rotating externally threaded base 541b within the second internally threaded hole, to adjust an amount of friction within joint 537. A split washer (not pictured) may be provided between a head of joint screw 541 and tab 539 or between both tabs 539 to inhibit unintended loosening of joint screw 541 from joint 537. In some embodiments, one end of the split washer may be fixed (e.g. via adhesive or welding) to the head of joint screw 541 to ensure that the split washer does not unintentionally become disconnected during assembly. Other similar devices, including other types of washers, may also be provided to help inhibit unintended loosening of joint screw 541 from joint 537. For example, a washer may be crimped over the unthreaded neck 541a between the head of joint screw 541 and the adjacent tab 539. In other embodiments, FIGS. 13A-13C illustrate a flexible link 629 according to another arrangement. As shown in FIG. 13A, flexible link 629 includes two flexible leaves 631 extending from a stem 633. Both leaves 631 include a hole extending therethrough, and a tightening screw 635a extends through both holes.

Tightening screw 635a is threadingly engaged with an internally threaded nut 635b set against or integrated with one of the leaves 631 opposite from a leaf 631 against which a head of tightening screw 635a is seated. A size or tightness of a socket defined between leaves 631 for rotatably accepting a ball 42 can therefore be adjusted by turning tightening screw 635a relative to nut 635b to adjust an amount of friction between ball 42 and the socket provided by leaves 631.

Turning to FIG. 13B, two flexible links 629 can be joined at a joint 637 shown in more detail, with flexible links 629 being rendered as translucent, in FIG. 13C. As shown in FIG. 13C, a pair of arms extends from each stem 633 away from leaves 631, and a pivot block 641 is disposed between the pairs of arms belonging to two flexible links 629. Two pivot pins 643 are disposed through corresponding holes in pivot block 641 at a right angle relative to one another and through corresponding holes in both pairs of arms. Joint 637 therefore allows flexible links 629 to move with two degrees of freedom relative to one another. In alternative arrangements of pivot block 641, however, pivot pins 643 may extend parallel to one another through corresponding holes of pivot block 641. In other embodiments, other types of joints such as a universal or gimbal joint may be provided to provide for additional degrees of rotation between the flexible links 629.

Figure 14B:
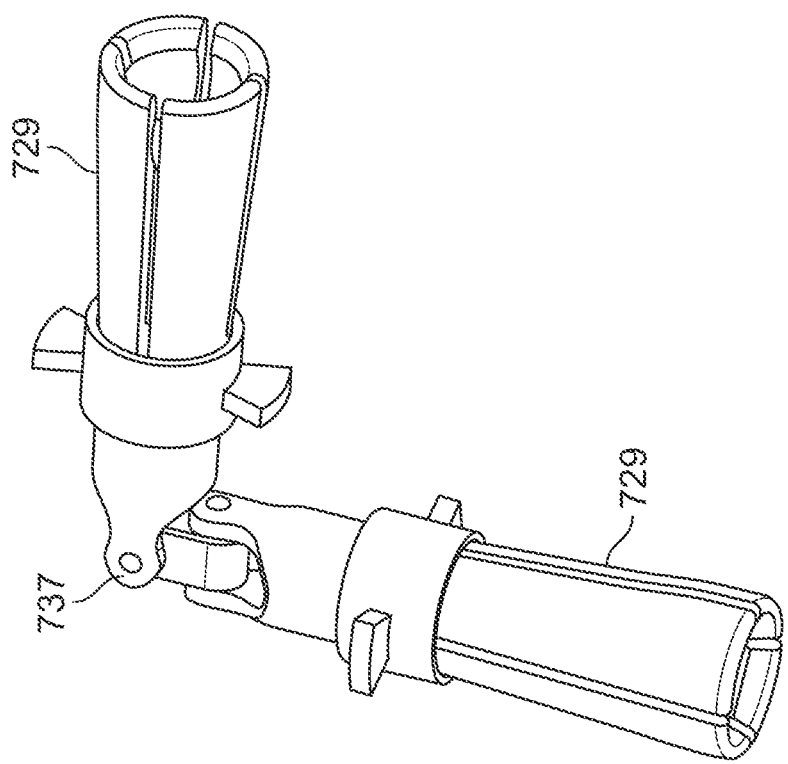
FIG. 14B is a perspective view of a hinge within the linkage of FIG. 14A.
Figure 14A:
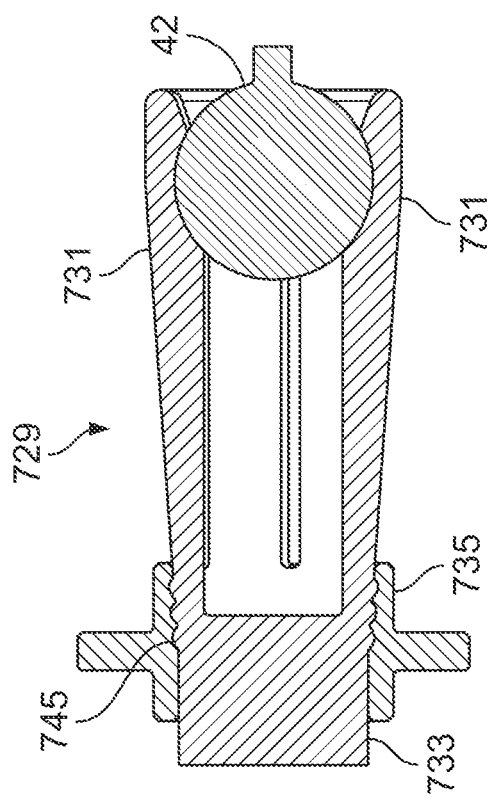
FIG. 14A is a cross-sectional view of a link of a resection guide according to another arrangement.

FIG. 14A depicts a flexible link 729 according to another arrangement. Like flexible link 529 of FIG. 12A, flexible link 729 includes four flexible leaves 731 extending from a stem 733 and defining a generally spherical socket for rotatably receiving ball 42 as illustrated. As with flexible link 529 of FIG. 12A, alternative arrangements of flexible link 729 of FIG. 14A with any number of leaves 731 greater than or equal to two are contemplated. A series of circular ribs 745 extends along stem 733 onto portions of leaves 731 adjoining stem 733, and a sleeve 735 is provided with a complementary internal series of ribs engaging ribs 745 of flexible link 729. Ribs 745 on flexible link 729 and the complementary ribs within sleeve 735 are not helical, but flexibility of flexible link 729 cooperates with flexibility of sleeve 735 to enable advancement of sleeve 745 in either direction across ribs 745 to adjust the freedom of leaves 731 to bend and to tighten the socket provided by leaves 731, thereby adjusting an amount of friction applied by the socket to ball 42.

FIG. 14B shows two flexible links 729 connected at a joint 737. Joint 737 of FIG. 14B is generally alike to joint 637 of FIGS. 13B and 13C, and thus provides two degrees of freedom. However, alternative arrangements of are contemplated wherein any of the differentiating features between any of flexible links 529, 629, 729 as illustrated in FIGS. 12A-14B in any manner are contemplated. Thus, flexible links according to FIG. 12A with a joint such as joints 637, 737 shown in FIGS. 13B, 13C, and 14B are contemplated, and flexible links according to FIGS. 13A and 13B with joints such as joint 537 as shown in FIGS. 12B and 12C are contemplated.

The links described above may be made of any material having structural properties sufficient to perform the above described functions of each individual link and interactions between links. Specifically, sleeves 44 and sockets 52 are constructed of material flexible enough to permit a user to reversibly force ball 42 into or out of track 46 or the spherical space within socket 52, but stiff enough to hold ball 42 stationary in the absence of manipulation by a user. Cutting block connector 30 is similarly constructed of material flexible enough to allow plug 64 to snap into or out of engagement with recess 70. Links having no flexing parts such as anchor 18 or barbell 26 may be constructed from the same material as, or a less flexible material than, links with sleeve 44, socket 52, or cutting block connector 30. In some examples, the links are constructed of titanium, steel, nitinol, or biocompatible plastics or polymers. In various further examples, links are constructed from a single material, or from different materials in different parts of links. In still further examples, links are constructed by additive manufacturing.

Any combination of the links described above may be used as appropriate for a given operation with the end goal of positioning the cutting block 20 (or 120, or 220, or 320) at a desired position and orientation relative to the proximal humerus so that the cutting block may be pinned (or otherwise fixed) to the humerus, and a cutting tool may be passed through the cutting slot of the cutting block to resect the humeral head in the desired position. For example, a surgeon may choose a combination of an appropriate number of links from the above described varieties of links and connect the links in sequence to create a linkage, which may be linkage 16 as illustrated in FIG. 1 or another linkage constructed from a plurality of the above described links. Linkages according to some arrangements include an anchor 18, 118, 218, 318, a cutting block 20, 120, 220, 320, and one or more other links to connect anchor 18, 118, 218, 318 to cutting block 20, 120, 220, 320. Anchor 18, 118, 220, 320 may be fixed to humeral head 12 by pins 22 and/or spikes 138 to connect the linkage to the patient. As described above, the links are pivotably connectable with enough friction to remain in a given respective orientation despite the influence of gravity unless actively manipulated by a user. In an initial positioning step, the linkage may therefore be manipulated after anchor 18, 118, 218, 318 is fixed to humeral head 12 to position cutting block 20, 120, 220, 320 near an intended resection plane of humerus 14, and cutting block 20, 120, 220, 320 will remain in that position. Alignment rod 38 may be keyed into aperture 68 in an appropriate orientation as described above before or after the initial positioning of cutting block 20, 120, 220, 320. The appropriate orientation of alignment rod 38 will correspond to an angle between the intended resection plane and the axis of humerus 14. Cutting block 20, 120, 220, 320 and the patient's arm may be respectively manipulated such that alignment rod 38 is aligned with humerus 14 and version rod 35 is aligned with the patient's forearm. After cutting block 20, 120, 220, 320 is manipulated such that slot 66 extends along the intended resection plane, cutting block 20, 120, 220, 320 may be immovably fixed to humerus 14 with, for example, pins 22. However, in other embodiments, the cutting block 20, 120, 220, 320 may be fixed to the humerus prior to checking alignment. After the cutting block 20, 120, 220, 320 is fixed to the humerus 14, some or all of the remaining portions of resection guide 10 may be disassembled and/or removed from the surgical site, which may provide for increased working space for the surgeon. A resection may be performed through slot 66 after cutting block 20, 120, 220, 320 is fixed to humerus 14.

As should be understood from the above description, the various anchors, cutting guides, and links described herein provide for a large degree of modularity in forming and using a resection guide such as those referred to above with numerals 10, 210, or 410. Any of the above described anchors, cutting guides, and links may be used in any configuration to provide a resection guide. Further, links may be produced having different combinations of features than the specific combinations illustrated and described above. For example, each cutting block 20, 120, 220, 320 described above is illustrated to include multiple unique features differentiating it from the other cutting blocks, but cutting blocks including any combination of the various features that differentiate the illustrated cutting blocks 20, 120, 220, 320 from each other are contemplated. In other words, the resection guide may be assembled differently from one patient to the next in order to best suit the patient's anatomy and surgical environment encountered by the surgeon. However, in most or all embodiments, the linkages described herein provide for six degrees of freedom of motion between the cutting block and the anchor, for example three linear degrees of freedom and three rotational degrees of freedom. This may help maximize the ability to desirably orient the cutting slot of the cutting guide in the exact position and orientation desired by the surgeon, preferably with the least necessary amount of components (e.g. intermediate linkages between the anchor and the cutting block) being utilized.

Although the invention herein has been described with reference to particular embodiments, it is to be understood that these embodiments are merely illustrative of the principles and applications of the present invention. For example, although the description above generally focuses on the use of resection guide 10 for a humerus, the resection guide 10 may be suitable for use, with or without modification, in other joints, such as for resecting a femoral head. It is therefore to be understood that numerous modifications may be made to the illustrative embodiments and that other arrangements may be devised without departing from the spirit and scope of the present invention as defined by the appended claims.

The invention claimed is:

1. A resection guide, comprising:
   an anchor having bone anchoring features;
   a cutting block having a cutting guide defined therein;
   a linkage flexibly connecting the cutting block to the anchor such that the cutting block has six degrees of freedom of motion relative to the anchor; and
   an alignment rod connectable to the cutting block, wherein the cutting block includes a connecting element whereby the alignment rod is connectable to the cutting block, the connecting element defining at least one discrete connected position for the alignment rod relative to the cutting block corresponding to an intended resection angle relative to a longitudinal axis of a bone to be cut.

2. The resection guide of claim 1, wherein the flexibility of the linkage includes a round element and a socket, wherein the socket is configured to receive the round element such that internal friction between the socket and round element enables the linkage to suspend the cutting block in opposition to gravity.

3. The resection guide of claim 1, wherein the linkage includes a chain of interconnected rigid links, each rigid link within the chain being of the same type and including both a round element and a socket configured to rotatably receive one of the round elements.

4. The resection guide of claim 1, wherein the linkage includes a link that further includes a plurality of flexible leaves defining a socket therebetween and a tightening element that is movable relative to the leaves to tighten the socket.

5. The resection guide of claim 4, wherein the leaves are elastically flexible such that a ball may be reversibly inserted into and removed from retention by the leaves.

6. The resection guide of claim 1, wherein the cutting guide includes a plurality of index holes at different positions relative to an aperture, and the alignment rod including an end engageable to the aperture and a boss engageable to one of the index holes.

7. The resection guide of claim 1, wherein the linkage includes at least a first type of link and a second type of link, wherein the first type of link differs from the second type of link.

8. The resection guide of claim 7, wherein the first type of link is modularly connectable to the second type of link, but the first type of link is not modularly connectable to another of the first type of link.

9. The resection guide of claim 8, wherein the second type of link includes at least one socket.

10. The resection guide of claim 8, wherein the first type of link is a barbell including a bar having two ends and a ball on each of the two ends of the bar, wherein the second type of link is a slider including a track defined by an element having a partial cylinder shape, the partial cylinder shape having an internal diameter providing an interference fit with either ball of the barbell.

11. The resection guide of claim 7, wherein the first type of link is a barbell including a bar having two ends and a ball on each of the two ends of the bar.

12. The resection guide of claim 1, wherein the linkage includes a first link including a peg and a second link including a bore sized to have an interference fit with the peg.

13. The resection guide of claim 1, wherein the connecting element is a cylindrical through-bore with two channels extending therefrom at equal but opposite angles relative to a slot of the cutting block, and the alignment rod includes a keyed portion, the keyed portion further including a key extending therefrom and insertable into the channels such that a connected position for the alignment rod relative to the cutting block wherein the key is inserted into either of the channels corresponds to the intended resection angle relative to the longitudinal axis of the bone to be cut.

14. The resection guide of claim 1, wherein the connecting element is a V-shaped aperture with two wings extending at equal but opposite angles relative to a slot of the cutting block, and the alignment rod includes a keyed portion, the keyed portion further including a key extending therefrom and a barrel having a rectangular cross-section, wherein the barrel and the key have a width equal to widths of the wings and wherein opposite faces of the barrel and the key are separated by a distance equal to lengths of the wings.

15. A method of performing a resection, comprising:
fixing an anchor to a patient;
positioning a cutting block into an intended position relative to the patient, the cutting block being connected to the anchor by a flexible linkage such that the cutting block has six degrees of freedom of motion relative to the anchor;
aligning or verifying alignment of an alignment rod connected to the cutting block relative to a longitudinal axis of a bone to be cut; and
cutting the bone through a cutting guide defined in the cutting block while the cutting block is in the intended position.

16. The method of claim 15, comprising fixing the cutting block to the patient after the positioning step and before the cutting step.

17. The method of claim 15, wherein the fixing step includes pushing spikes extending from the anchor into a portion of bone to be resected.

\* \* \* \* \*